United States Patent
Birkett

(12) 
(10) Patent No.: US 6,231,864 B1
(45) Date of Patent: May 15, 2001

(54) STRATEGICALLY MODIFIED HEPATITIS B CORE PROTEINS AND THEIR DERIVATIVES

(75) Inventor: Ashley J. Birkett, Solana Beach, CA (US)

(73) Assignee: Immune Complex Corporation, San Diego, CA (US)

( * ) Notice: Subject to any disclaimer, the term of this patent is extended or adjusted under 35 U.S.C. 154(b) by 0 days.

(21) Appl. No.: 09/248,588

(22) Filed: Feb. 11, 1999

Related U.S. Application Data

(60) Provisional application No. 60/074,537, filed on Feb. 12, 1998.

(51) Int. Cl.[7] .......................... A61K 39/29; A61K 39/385

(52) U.S. Cl. ..................................... 424/189.1; 424/192.1; 424/194.1; 424/196.11; 424/201.1; 424/202.1; 424/227.1; 530/350; 530/402; 530/403

(58) Field of Search ............................. 424/189.1, 192.1, 424/194.1, 196.11, 201.1, 202.1, 227.1; 530/350, 402, 403

(56) References Cited

U.S. PATENT DOCUMENTS

| | | | |
|---|---|---|---|
| 4,710,463 | 12/1987 | Murray et al. ........................ | 435/68 |
| 4,818,527 * | 4/1989 | Thornton et al. ...................... | 424/88 |
| 4,882,145 | 11/1989 | Thornton et al. ...................... | 424/88 |
| 5,143,726 | 9/1992 | Thornton et al. ...................... | 424/88 |

FOREIGN PATENT DOCUMENTS

| | | | |
|---|---|---|---|
| 385610 B1 * | 9/1990 | (EP) . | |
| 0 421 635 B1 | 7/1995 | (EP) ............................ | A61K/39/295 |

OTHER PUBLICATIONS

Schödel et al., Hybrid hepatitis B core antigen as a vaccine carrier moiety: I. Presentation of foreign epitopes. Journal of Biotechnology 44:91–96, 1996.*
F. Galibert, et al., Nature, 281:646–650 (1979).
J.R. Lamb et al., J. Immunol., 129:1465 (1982).
P.A. Scherle et al., J. Exp. Med., 164:1114 (1986).
P. Lake et al., Cold Spring Harbor Symp. Quant. Biol., 41:589 (1976).
J.G. Sutcliffe et al., Nature, 287:801 (1980).
R.A. Lerner et al., Proc. Natl. Acad. Sci. USA, 78:3403 (1981).
Gerin et al., Proc. Natl. Acad. Sci. USA, 80:2365 (1983).
F. Delpeyroux et al., Science, 233:472–475 (1986).
B.E. Clarke et al. Vaccines 91:313–318 (1991).
F. Schödel et al. J. Virol. 66(1):106–114 (1992).
D.R. Milich et al., Science, 234:1398–1401 (1986).
J.F. Conway et al., Nature, 386:91–94 (1997).
B. Bottcher et al., Nature, 386:88–91 (1997).
G. Colucci et al., J. Immunol., 141:4376–4380 (1988).
J.Salfeld et al. J. Virol. 63:798 (1989).
P. Pumpens et al., Intervirology, 38:63–74 (1995).
R. Ulrich, et al., Advances in Virus Research, 50:141–192 (1998).

* cited by examiner

*Primary Examiner*—Donna C. Wortman
(74) *Attorney, Agent, or Firm*—Welsh & Katz, Ltd.

(57) ABSTRACT

A strategically modified hepatitis B core protein is described, where an insert is provided, preferably in an immunodominant region of the nucleocapsid protein, containing a chemically reactive amino acid residue. The modified hepatitis B core protein or its aggregated nucleocapsid protein particles can be pendently linked to a hapten to form a modified nucleocapsid conjugate. Such a conjugate is useful in the preparation of vaccines or antibodies. The modified hepatitis B core protein can also be modified to include a T cell epitope.

22 Claims, 1 Drawing Sheet

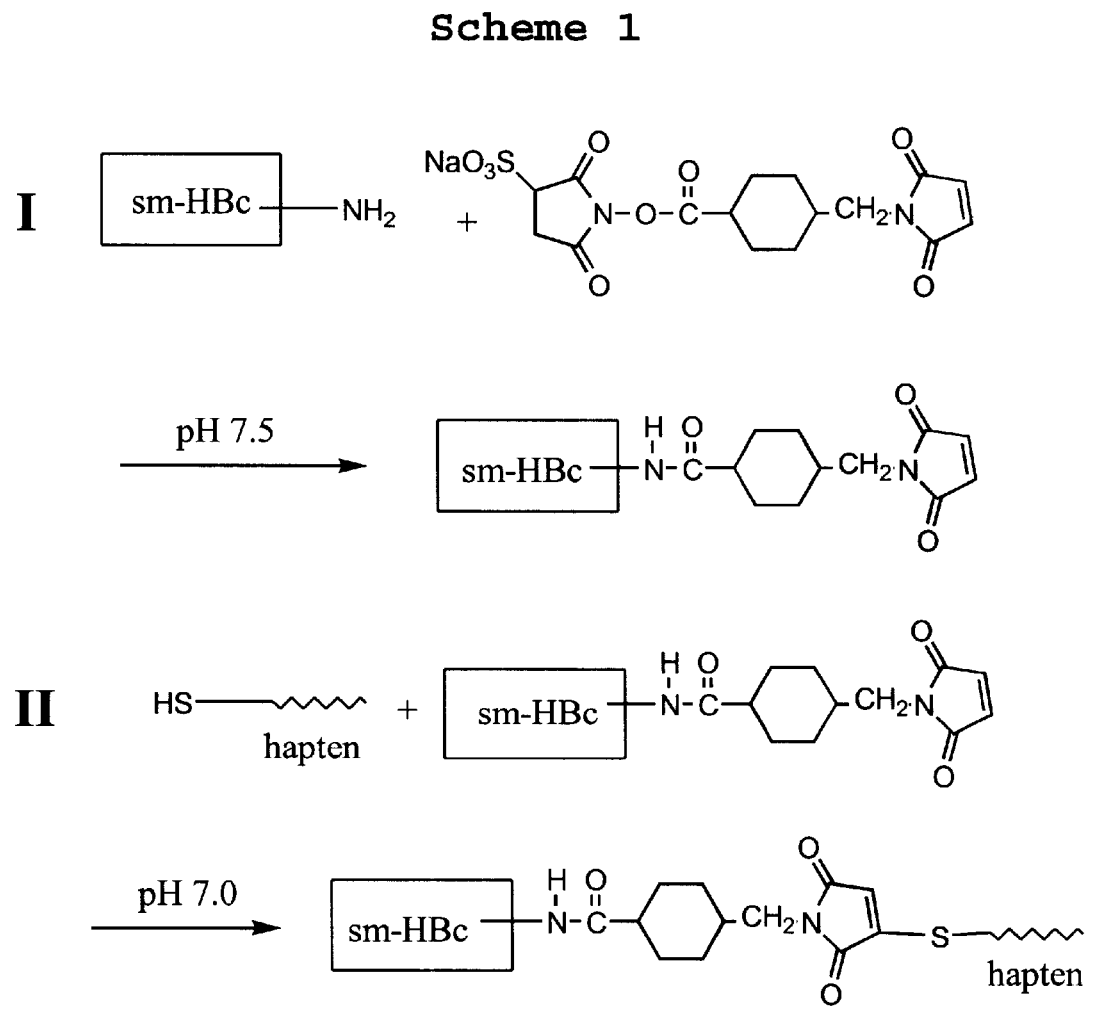

Scheme 1

STRATEGICALLY MODIFIED HEPATITIS B CORE PROTEINS AND THEIR DERIVATIVES

CROSS REFERENCE TO A RELATED APPLICATION

This application is a continuation-in-part of U.S. Provisional Application No. 60/074,537, filed Feb. 12, 1998.

TECHNICAL FIELD

The present invention relates to the intersection of the fields of immunology and protein engineering, and particularly to carrier proteins, and more particularly to a hepadnavirus nucleocapsid protein strategically modified with an inserted chemically-reactive amino acid residue, a pendently-linked hapten conjugate of that hepadnavirus nucleocapsid protein and to an immunogenic particle comprised of those conjugates.

BACKGROUND OF THE INVENTION

It is known that antibodies can be raised to a small molecule by using a large immunogenic protein molecule as a carrier. The small molecule that derives enhanced immunogenicity by being conjugated to the carrier is called a hapten. The phenomenon of a relatively large molecule potentiating the immunogenicity of a small molecular entity to which it is attached is known in the art as the "carrier effect."

The portion of an immunogen recognized by the helper T cell (Th cell) is the T cell determinant or epitope. The portion of an immunogen that is bound by antibody is the B cell determinant or epitope. Carrier effects can be defined as immunity to one determinant, the "helper" or T ($T_h$) cell determinant, of a multideterminant immunogen enhancing the immune response to another determinant, the B cell determinant.

It is now well established that most immunogens require T cell help to induce B cells to produce antibodies. Thus, $T_h$ cells, by recognizing helper determinants on the immunogen help B cells to make antibody against the immunogen.

The antigenic determinants recognized by T helper cells ($T_h$) and B cells must be associated to form a single molecular entity, but they do not have to be covalently linked. See, Russel et al., *Nature,* 280:147 (1979), Lamb et al., *J. Immunol.,* 129:1465 (1982), Scherle et al., *J. Exp. Med.,* 164:1114 (1986) and Lake et al., *Cold Spring Harbor Symp. Quant. Biol.,* 41:589 (1976). Some immunogens do not require T cell help to induce antibody formation, these are T-independent antigens.

A pathogen-related protein can be immunologically mimicked by the production of a synthetic polypeptide whose sequence corresponds to that of a determinant of the pathogen. Such polypeptide immunogens are reported by Sutcliffe et al., *Nature,* 287:801 (1980), and Lerner et al., *Proc. Natl. Acad. Sci. USA,* 78:3403 (1981).

Gerin et al., *Proc. Natl. Acad. Sci. USA,* 80:2365 (1983), showed limited protection of chimpanzees from hepatitis B virus upon immunization with carrier-bound synthetic polypeptides having amino acid residue sequences that correspond to the sequence of a determinant portion of HBsAg; in particular, residues 110–137 of the "S" (surface) region. However, the carrier protein used in those studies was keyhole limpet hemocyanin (KLH), a T cell-dependent carrier that is not fit for use in medical applications to humans because it is a source of irritation that leads to severe inflammation.

T cell-stimulating carrier proteins capable of enhancing the immunogenicity of haptens that do not produce unacceptable side effects in human subjects are often immunogenic natural proteins. For example, tetanus toxoid (TT) has been frequently used when a carrier suitable for human administration was needed. However, the use of tetanus toxoid as a carrier was restricted due to problems with dosage limitations and risk of sensitization to the toxoid itself. In addition, an epitope-specific suppression of response to the carried hapten can occur in individuals already immunized against tetanus.

The hepatitis B surface protein has been proposed as a carrier for heterologous epitopes. Delpeyroux et al., *Science,* 233:472–475 (1986), reported the use of the HBV surface protein (S protein) as a carrier for a poliovirus polypeptide hapten. Those investigators constructed a recombinant deoxyribonucleic acid (DNA) protein expression vehicle that produces a fusion protein, designated HBsPolioAg, capable of forming particles closely resembling authentic 22-nanometer HBsAg particles. HBsPolioAg consists of HBV S protein having an 11 amino acid residue sequence insert corresponding to amino acids 93–103 of capsid protein VPI of poliovirus type 1 (Mahoney strain).

Hepadnavirus nucleocapsid proteins have been used as hapten carriers. Heterologous immunogenic peptide sequences inserted internally in the hepatitis B core, expressed as fusion particles, elicited very high immune responses in immunized animals in the absence of adjuvants. B. E. Clarke et al. *Vaccines* 91:313–318 (1991); F. Schödel et al. *J. Virol.* 66(1):106–114 (1992). U.S. Pat. Nos. 4,818,527, 4,882,145, and 5,143,726, the disclosures of which are incorporated herein by reference, describe the use of the carrier effect with hepatitis B virus nucleocapsid protein to enhance the immunogenicity of an operatively linked polypeptide hapten. Those patents describe the linking of a polypeptide hapten to hepatitis B virus nucleocapsid protein through an amino acid residue side chain that occurs naturally in the hepatitis B nucleocapsid protein sequence.

Hepadnavirus nucleocapsid proteins are fairly well studied. SEQ ID NOs:1 and 2 are the DNA and amino acid sequences of the human hepatitis B core protein (HBc), subtype ayw, as described in U.S. Pat. Nos. 4,818,527, 4,882,145, and 5,143,726. Other hepadnavirus nucleocapsid protein sequences are also known in the art, see e.g. SEQ ID NOs: 3–13.

There are reasons to select hepadnavirus nucleocapsid proteins as a carrier over other carriers used in the art, such as keyhole limpet hemocyanin (KLH), BCG, tetanus toxoid and diphtheria toxoid. KLH, BCG, tetanus toxoid and diphtheria toxoid are non-particulate, whereas hepadnavirus nucleocapsid proteins tend to aggregate into "particles". HBc particles tend to have a higher immunogenicity than hepatitis B surface antigen (HBsAg) particles. D. R. Milich et al., *Science,* 234:1398–1401 (1986). HBc is both a T cell-independent and a T cell-dependent immunogen. Id. HBc is one of the most immunogenic proteins known. Almost all hepatitis B-infected people develop a powerful immune response to core. J. H. Hoofnagle, *Semin. Liver Dis.,* 1(1):7–14 (1981). HBc can provide universal responsiveness, irrespective of genetic background. Id. HBc directly activates T cells. HBc elicits strong $T_h$ cell responses. HBc is efficiently processed and presented by antigen-presenting cells. Due to the inherently high immunogenicity of HBc, complex adjuvants are typically not required, for example, the common and inexpensive alum is sufficient.

The family hepadnaviridae is a family of enveloped animal viruses with a core of DNA that cause hepatitis B in humans. The hepadnaviridae are not responsible for human hepatitis A (a single-stranded RNA enterovirus), human hepatitis C (Flaviridae family of single stranded RNA virus), or human hepatitis D (a closed circular negative-sense RNA satellite virus, "delta virus", that requires hepatitis B virus for replication). The hepadnaviridae family includes hepatitis viruses of other species, e.g. woodchuck, duck, ground squirrel, and heron, in addition to human and simian hepatitis B. Hepatitis B (HB) used hereinafter refers to the family hepadnaviridae, unless the discussion is referring to a specific example.

Hepatitis B core protein monomers self-assemble into stable aggregates known as hepatitis B core protein particles (HBc particles). For example, human HBc particles are 27 nanometers (nm) in diameter. Conway et al., *Nature*, 386:91–94 (1997), describe the structure of human HBc particles at 9 Ångstrom resolution, as determined from cryo-electron micrographs. Bottcher et al., *Nature*, 386:88–91 (1997), describe the polypeptide fold for the human HBc monomers, and provide an approximate numbering scheme for the amino acid residues at which alpha helical regions and their linking loop regions form. Bottcher et al. propose a loop from about residues 78 to 82 of the hepatitis B core protein.

Using synthetic peptides and monoclonal antibodies, the immunodominant loop region of HBc was mapped to about amino acid residues 75 to 83. G. Colucci et al., *J. Immunol.*, 141:4376–4380 (1988). Two immunodominant linear epitopes were reported by other workers at amino acid residues 75 to 85 and 130 to 140. Salfeld et al. *J. Virol.* 63:798 (1989).

Insertion mutants of the hepatitis B core protein still are able to form core particles when foreign epitopes are cloned into the immunodominant loop region of HBc. P. Pumpens et al., *Intervirology*, 38:63–74 (1995). The HBc fusion proteins form particles in prokaryotic and eukaryotic expression systems. Id.

The ability to use a protein as a carrier for a pendently-linked hapten depends upon several factors that have been studied with respect to HBc. Chemically-reactive amino acid side chains, such as lysine (K), aspartic acid (D), glutamic acid (E), and reduced cysteine residues (C), provide functional groups that can be useful for modifying polypeptides.

The hepatitis B core protein sequence has several chemically-reactive amino acid side chains in the native sequence. Core has three primary amino groups, one at the amino terminus, and two lysine residues (K5 and K96), along with four cysteine residues (C48, C61, C107 and C183). There are several carboxylic acid groups, D (2, 4, 22, 29, 32, 78, 83) and E (8, 14, 40, 43, 46, 64, 77, 113, 117, 145, 179) and the carboxy terminus.

However, the native, unmodified hepatitis B core protein particle does not exhibit appreciable chemical reactivity of the amino acid side chains in the native sequence. The chemical reactivity of an amino acid side chain in a protein depends upon the nature of the amino acid side chain, and its environment in the folded protein.

As is discussed in detail hereinafter, it has now been found that the problem of low reactivity of the amino acid side chains in native hepatitis B nucleocapsid protein can be overcome by inserting a chemically-reactive amino acid side chain into the HBc protein sequence. A strategically modified hepadnavirus core protein particle of the present invention exhibits substantially enhanced reactivity toward derivatization of HBc particles with chemically linked haptens, and provides enhanced immunogenicity to those linked haptens.

These modified HBc proteins and their pendently-linked hapten conjugate derivatives are discussed in the disclosure that follows.

BRIEF SUMMARY OF THE INVENTION

The present invention relates to a strategically modified hepatitis B core (HBc) protein that is linked to a pendent hapten through chemically-reactive amino acid residue inserted into the HBc sequence. The contemplated strategic modification of HBc is an insert mutation of the HBc protein. A contemplated insert is 1 to about 40 amino acid residues in length, preferably 1 to 10 amino acid residues in length, and includes a chemically-reactive amino acid residue.

The insert is provided to the region corresponding to amino acid residues about 50 to about 100 of the hepatitis B core protein sequence shown in SEQ ID NO:2. The preferred region of insertion corresponds to the hepatitis B core protein immunodominant loop region at about amino acid residue 70 to about 90, more preferably the loop tip region at about amino acid 78 to about 82 and most preferably at amino acid 78 to amino acid 80.

Such an introduced chemically-reactive amino acid residue is characterized in that it has a chemically-reactive side chain that provides a chemical group for pendently linking the strategically modified HBc to the hapten. Typically, the chemically-reactive amino acid residue is a lysine, cysteine, or histidine residue or a carboxyl-containing residue such as aspartic acid or glutamic acid, preferably lysine or a carboxyl-containing residue, and most preferably lysine.

The hapten bonded to the chemically-reactive amino acid residue is any compound of interest for generating an immune response, and is typically a B cell determinant. Preferably, the hapten is a polypeptide hapten, a carbohydrate hapten, or a non-peptidal/non-saccharidal (chemical) hapten. In one embodiment of the invention, the hapten is a pathogen-related hapten, such as a B cell determinant of a pathogen.

In another embodiment of a strategically modified hepatitis B core protein conjugate, the strategically modified hepatitis B core protein also has a T cell stimulating amino acid residue sequence operatively linked to the carboxy terminus of the hepatitis B core amino acid sequence. Preferably, both the hapten and the T cell stimulating amino acid residue sequence are pathogen-related, most preferably, both are related to (from) the same pathogen.

In the above embodiment of the invention, the response to a B cell epitope is boosted by also providing the T helper ($T_h$) cell determinant. In this preferred embodiment of the invention, such a $T_h$ cell determinant is from the same pathogen as the B cell determinant hapten that is pendently linked to the strategically modified hepatitis B core protein in order to provide pathogen-specific T cell memory in addition to the hepatitis B core protein antigen-specific T cell memory.

A strategically modified hepatitis B core protein conjugate contains a hapten that is pendently linked to a strategically modified hepatitis B core protein. Looked at differently, a before-described strategically modified hepatitis B core protein can be considered to have three peptide-linked domains, I, II and III (numbered consecutively from the amino terminus). Domain I comprises a sequence that corresponds to residues numbered about 10 to 50 of the amino acid sequence of hepatitis B core protein of SEQ ID NO:2, and preferably corresponds to residues numbered 1 to 50 of that sequence. Domain II is bonded to the carboxy terminal residue of Domain I. Domain II corresponds to residues numbered 50 to 100 of the amino acid sequence of hepatitis B core protein of SEQ ID NO:2. Domain III comprises a sequence that is bonded to the carboxy terminal residue of Domain II. Domain III corresponds to residues numbered 100 to about 140 of the amino acid sequence of hepatitis B core protein, and preferably corresponds to residues numbered 100 to about 149 of that sequence.

In an embodiment of the invention discussed before, a strategically modified hepatitis B core protein additionally has a Domain IV exogenous to HBc that is peptide-bonded to the carboxy terminal residue of Domain III to provide a fusion protein. Domain IV is a T cell epitope.

A strategically modified hepatitis B core protein particle of the invention is made of assembled heptatitis B core protein where a plurality of the subunits are strategically modified hepatitis B core protein subunits. Also contemplated is a particle comprised of a mixture of strategically modified hepatitis B core protein subunits and other hepatitis B core protein subunits.

A contemplated strategically modified hepatitis B core protein particle conjugate is comprised of assembled hepatitis B core protein subunits where a plurality of the subunits are strategically modified hepatitis B core protein subunits. In this embodiment, a hapten is pendently linked to a hepatitis B core protein subunit. Preferably, the hapten is pathogen-related. As above, a T cell stimulating amino acid residue sequence can be peptide-bonded to the carboxy terminal residue of the sequence corresponding to hepatitis B core protein. Preferably that pathogen-related T cell determinant is related to the same pathogen as the pathogen-related hapten.

A strategically modified hepatitis B core protein particle conjugate of the invention has pendently-linked hapten. In a contemplated embodiment of the particle conjugate, the particle is made up of a mixture of strategically modified hepatitis B core protein subunits having pendently-linked haptens, and other hepatitis B core protein subunits. In one embodiment, about 0.1 to about 0.5 of the strategically modified hepatitis B core protein subunits are pendently linked to a hapten. Also contemplated is a particle conjugate that is made up of a mixture of strategically modified hepatitis B core protein subunits and other hepatitis B core protein subunits.

A before-described strategically modified hepatitis B core protein of the invention includes a peptide insert containing a chemically-reactive amino acid residue. That insert can be, but is typically not, itself a separate B cell antigenic determinant, although some B cell immunogenicity of the insert can be exhibited merely because of the placement of the insert into the HBc protein or particle. Such an insert can be and in some embodiments is a T cell epitope. Placement of an insert into the HBc loop region greatly diminishes the HBc immunogenicity and antigenicity of the resulting molecule.

An inoculum of the invention comprises an immunogenic amount of the strategically modified hepatitis B core protein conjugate of the invention. When the pendently-linked hapten is a pathogen-related hapten, the inoculum can be used as a vaccine to protect a mammal treated with the inoculum from that pathogen. Thus, in one embodiment of the invention, a strategically modified hepatitis B core protein conjugate is used as a vaccine to provide protection against the pathogen from which the hapten is derived. More preferably, the inoculum is comprised of strategically modified hepatitis B core protein particle conjugate as the immunogen.

The present invention has several benefits and advantages.

One benefit of a contemplated modified HBc protein is that the protein can be derivatized while in the aggregated form of HBc particles.

An advantage of the invention is that the modified HBc protein displays appreciably enhanced chemical reactivity toward derivatization, as compared to use of the N-terminal primary amine, for example.

Another benefit of a contemplated modified HBc protein is that the chemistry of derivatization of such side chains is well-studied, straightforward and relatively predictable.

Another advantage of a contemplated modified HBc protein is that it enhances the immunologic response to the conjugated hapten with which it is derivatized.

Yet another benefit of a contemplated modified HBc protein is that it is unlikely to produce undesirable immunologic side effects in humans.

Still further benefits and advantages of the invention will be apparent to the skilled worker from the discussion that follows.

BRIEF DESCRIPTION OF THE DRAWINGS

In the figure forming a portion of this disclosure Scheme 1 illustrates a reaction sequence for pendently linking a hapten to a strategically modified hepatitis B core protein (sm-HBc) particle using sulpho-succinimidyl 4-(N-maleimidomethyl) cyclohexane 1-carboxylate (sulpho-SMCC). The sm-HBc particle is depicted as a box having (for purposes of clarity of the figure) a single pendent amino group.

DETAILED DESCRIPTION OF THE INVENTION

A. Definitions

The term "antibody" refers to a molecule that is a member of a family of glycosylated proteins called immunoglobulins, which can specifically combine with an antigen.

The word "antigen" has been used historically to designate an entity that is bound by an antibody, and also to designate the entity that induces the production of the antibody. More current usage limits the meaning of antigen to that entity bound by an antibody, whereas the word "immunogen" is used for the entity that induces antibody production. Where an entity discussed herein is both immunogenic and antigenic, reference to it as either an immunogen or antigen will typically be made according to its intended utility.

The word "hapten" is used to describe molecules that are capable of stimulating an immune response (e.g., production of antibody) when chemically coupled to a protein carrier. The word is often used for small nonantigenic molecules in the art, but herein, it merely refers to the molecule that is to be pendently linked to the carrier protein, even if it is antigenic or not small.

"Antigenic determinant" refers to the actual structural portion of the antigen that is immunologically bound by an antibody combining site or T cell receptor. The term is also used interchangeably with "epitope."

The noun "conjugate" as used herein refers to a molecule formed from a hapten pendently linked through an amino acid residue side chain to a carrier.

The term "conservative substitution" as used herein denotes that one amino acid residue has been replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that antibodies raised to such a polypeptide also immunoreact with the corresponding polypeptide having the unsubstituted amino acid.

The term "corresponds" in its various grammatical forms as used in relation to peptide sequences means the peptide sequence described plus or minus up to three amino acid residues at either or both of the amino- and carboxy-termini and containing only conservative substitutions in particular amino acid residues along the polypeptide sequence. "Epitope" refers to that portion of a molecule that is specifically bound by a T cell antigen receptor or an antibody combining site.

"Epitope" and "determinant" are used interchangeably.

As used herein, the term "fusion protein" designates at least two amino acid residue sequences not normally found linked together in nature operatively linked together end-to-end (head-to-tail) by a peptide bond between their respective terminal amino acid residues.

The phrase "hepatitis B" as used here refers in its broadest context to any member of the family hepadnaviridae, a family of enveloped DNA-containing animal viruses that can cause hepatitis B in human.

The phrase "HBc" as used here refers to T cell stimulating proteins having an amino acid residue sequence that corresponds to an amino acid residue sequence encoded by the hepatitis B virus (HBV) nucleocapsid protein gene. An exemplary well-known naturally occurring protein encoded by the human HBV nucleocapsid gene is the "core" protein, subtype ayw, having the biological sequences of SEQ ID NOs: 1 and 2. Galibert, et al., Nature 281:646 (1979). HBeAg protein, the precursor to HBc, includes the sequence of the hepatitis B core protein and a "pre-core" sequence at the amino terminus thereof, as shown in SEQ ID NOs: 8 and 9 in the case of a ground squirrel hepatitis B nucleocapsid gene. The core protein sequence begins at amino acid position 31 therein, thus corresponding to amino acid residue number 1 of SEQ ID NO:2. The sequences for other hepatitis B core proteins are known in the art. Human hepatitis B virus core protein subtype adr is provided in SEQ ID NOs: 3 and 4, and subtype adw is provided in SEQ ID NOs: 5 and 6. Ono et al., Nucl. Acids Res. 11:1747 (1983). Sequences are also provided for woodchuck hepatitis B core protein at SEQ ID NO:7 [Schödel et al., Adv. Viral Oncol. 8:73–102 (1989)], ground squirrel at SEQ ID NOs:8 and 9, heron at SEQ ID NOs:10 and 11, and duck at SEQ ID NOs:12 and 13. For clarity, the amino acid numbering system shown in SEQ ID NOs:1 and 2 with respect to human hepatitis B core protein subtype ayw is used as a benchmark herein. Other HBc sequences can be aligned with that sequence using standard biological sequence alignment programs and protocols to determine the amino acid residues that "correspond to the hepatitis B core protein sequence of SEQ ID NO:2", see e.g. Schodel et al., Adv. Viral Oncol. 8:73–102 (1989).

If reference is made to a polypeptide portion of any of the above described naturally occurring HBV nucleocapsid gene encoded proteins, that reference is explicit, either by stating, for example, that a T cell stimulating portion of the particular protein is referred to or by explicitly designating the particular portion of the sequence, as by indication of the included amino acid residue positions.

The term "immunoreact" in its various forms means specific binding between an antigen as a ligand and a molecule containing an antibody combining site such as a Fab portion of a whole antibody.

The phrase "operatively linked" as used herein means that the linkage does not interfere with the ability of either of the linked groups to function as described; e.g., to function as a T or B cell determinant.

The phrase "pendently linked" refers to a single linkage, either direct or via a bridge, from a HBc protein to another molecule at other than the amino or carboxy termini. The phrase is used herein to describe the linkage between a hapten and a chemically-reactive amino acid side chain of a strategically modified hepatitis B core protein.

"Macromolecular assembly" refers to a non-covalently bonded aggregate of protein subunits. Typically in this invention, the protein subunit is a strategically modified hepatitis B core protein monomer. As described in more detail hereinafter, those core protein monomers usually self-assemble into spherical "core particles" having either 90 or 120 core protein dimers (a total of 180 or 240 core protein subunits). A spherical core particle is an example of a macromolecular assembly.

The phrase "pathogen-related" as used herein designates a B cell or T cell immunogen that is capable of inducing the production of antibodies that immunoreact with a pathogen in native form. Exemplary pathogen-related B cell and T cell immunogens are illustrated hereinafter.

The words "polypeptide" and "peptide" as used interchangeably throughout the specification and designate a linear series of amino acid residues connected one to the other by peptide bonds between the alpha-amino and carboxy groups of adjacent amino acids. Polypeptides can be variety of lengths, either in their neutral (uncharged) forms or in forms which are salts, and either free of modifications such as glycosylation, side chain oxidation, or phosphorylation or containing these modifications. It is well understood in the art that amino acid residue sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acid side chains, such as glycosyl units, lipids, or inorganic ions such as phosphates, as well as modifications relating to chemical conversions of the chains, such as oxidation of sulfhydryl groups. Thus, "polypeptide" or its equivalent terms is intended to include the appropriate amino acid residue sequence referenced, subject to those of the foregoing modifications which do not destroy its functionality. A peptide or polypeptide used as a hapten typically contains fewer than 70 amino acid residues, and more typically contains a linear chain of about 5 to about 40 amino acid residues, and more preferably about 10 to about 25 residues. It is noted that a contemplated polypeptide hapten can be longer than 70 residues, but such a polypeptide is shorter than the naturally occurring protein that shares its sequence.

The word "protein" designates a polypeptide having about 70 or more amino acid residues, and is a naturally occurring entity.

The words "secrete" and "produce" are often used interchangeably in the art as to cells from which antibody molecules are obtained. Cells that produce antibodies may, however, not secrete those molecules into their environment. Herein, the antibody molecules are secreted and are obtained from the blood stream (humoral antibody). Nevertheless, antibodies are generally referred to as being "produced" in keeping with the phrase utilized in the art.

All amino acid residues identified herein are in the natural or L-configuration. In keeping with standard polypeptide nomenclature, [*J. Biol. Chem.*, 243, 3557–59 (1969)], abbreviations for amino acid residues are as shown in the following Table of Correspondence, Table 1.

TABLE 1

TABLE OF CORRESPONDENCE SYMBOL

| 1-Letter | 3-Letter | AMINO ACID |
|---|---|---|
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| Z | Glx | L-qlutamic acid or L-glutamine |
| W | Trp | L-tryptophan |
| R | Arg | L-arginine |
| D | Asp | L-aspartic acid |
| N | Asn | L-asparagine |
| B | Asx | L-aspartic acid or L-asparagine |
| C | Cys | L-cysteine |

B. Strategically Modified Hepatitis B Core Protein

The present invention contemplates a strategically modified hepadnaviridae core ("HBc") protein that has an inserted chemically reactive amino acid residue for pendently linking with haptens such as polypeptides and carbohydrates. The strategic modification of the invention is the insertion of 1 to about 40 amino acid residues including a chemically-reactive amino acid residue into the hepatitis B core protein sequence in the region corresponding to amino acid residues 50 to 100 of the HBc sequence of SEQ ID NO:2. Such an introduced chemically-reactive amino acid residue has a side-chain that provides a functional group for pendently linking a hapten to the strategically modified carrier.

Hepadnaviridae have a nucleocapsid, or core, surrounded by a lipid envelope containing surface proteins. The nucleocapsid is a generally spherical aggregate of core proteins ("core antigen", HBcAg) dimers. In vitro, the hepatitis B core protein self-assembles into "particles", spherical shells of icosahedral symmetry made up of 90 or 120 hepatitis B core protein dimers, thus 180 or 240 protein subunits. The particles are about 280 or 310 Ångstroms in diameter, respectively. B. Bottcher et al., *Nature,* 386:88–91 (1997); J. F. Conway et al. *Nature* 386:91–94 (1997).

A contemplated strategically modified hepatitis B core protein also forms a macromolecular assembly. Such a particle can be present in the form of 180 or 240 protein subunits, although it does not have to be such a 90 or 120 dimer.

Hybrid core proteins with exogenous amino acid residues inserted in the region near amino acid residue 80 are reported to assemble into regular shells, even with inserts as large as 46 amino acids in length. A. I. Brown et al., *Vaccine,* 9:595–601 (1991); F. Schödel et al., *J. Virol.,* 66:106–114 (1992).

The hepadnaviridae core protein sequence used as a benchmark sequence herein is that of the human hepatitis B core protein, subtype ayw, shown in SEQ ID NOs:1 and 2. Other subtypes of the human hepatitis B virus are known. SEQ ID Nos: 3 and 4 are human HBc, subtype adr, and SEQ ID NOs:5 and 6 are HBc subtype adw. The sequences of various animal hepatitis core proteins are also published. The biological sequence of duck hepatitis core protein is disclosed herein as SEQ ID NO:12 and 13; a portion of the ground squirrel hepatitis nucleocapsid gene is at SEQ ID NO:8 and 9; woodchuck hepatitis core is at SEQ ID NO:7 and heron hepatitis core at SEQ ID NOs:10 and 11. Exemplary animal hepatitis B core proteins are aligned with human hepatitis B core protein by F. Schödel et al., *Adv. Viral Oncology* 8:73–102 (1989).

i. Strategic Modification of the Core Protein

The present invention contemplates a strategically modified hepatitis B core protein conjugate that comprises a hapten that is pendently linked to a strategically modified hepatitis B core protein (HBc). The strategically modified hepatitis B core protein itself comprises an amino acid sequence corresponding to the hepatitis B core protein amino acid sequence of SEQ ID NO:2 including the amino acid residues numbered about 10 to about 140 of that sequence. That HBc amino acid residue sequence additionally contains an exogenous amino acid residue insert in the region corresponding to amino acid residues numbered about 50 to about 100 from the HBc amino terminus, wherein the exogenous insert (i) is 1 to about 40 amino acid residues in length, and (ii) contains a chemically-reactive amino acid residue. The hapten is pendently linked to the strategically modified HBc protein by means of a chemically-reactive amino acid residue present in the insert.

It is preferred that residues 1 through 10 of SEQ ID NO:2 be present in the strategically modified HBc protein molecule. It is further preferred when any residue is absent or deleted from position 1 to 10 that those residues be deleted in sequence and that the remaining residues be present in sequence. Thus, if a five residue deletion were contemplated, the deleted residues would be numbered 1–5, leaving residues 6 through the desired HBc carboxy terminus present, plus the insert.

It is similarly preferred that residues numbered about position 140 through 149 of SEQ ID NO:2 be present in a strategically modified HBc protein molecule. As noted elsewhere herein, the region of HBc numbered 150 through the carboxy terminus contains a plurality of arginine residues. Those residues bind nucleic acids on purification of HBc particles after expression, and the sequence containing those residues is preferably omitted from a strategically modified HBc protein molecule. As was the case with the residues of positions 1 through 10, it is preferred that residues between about position 140 and 149 be present and correspondingly absent in a sequential manner. Thus, where the carboxy terminal residue corresponds to the residue of position 146, the residues of positions 141–145 are also present and those of 147–149 are absent. Most preferably, a contemplated HBc sequence is that shown in SEQ ID NO:2 from position 1 through position 149, plus the sequence of the insert.

The insert can be placed within the HBc sequence in the region of positions numbered about 50 through about 100, as already noted. Preferably, the insert is present in the region corresponding to amino acid residues numbered about 70 to about 90. More preferably, the insert is present in the region corresponding to amino acid residues numbered 78 to 82. Most preferably, the insert is located in the region corresponding to residues numbered 78 through 80.

A strategically modified hepatitis B core protein of the invention has from 1 to about 40 amino acid residues inserted. Preferably, the insert is 1 to 10 amino acid residues in length. The insert contains a chemically-reactive amino acid residue. The insertion of more than one chemically-reactive amino acid residue is also contemplated.

It is contemplated that restriction endonuclease sites be provided in the gene construct for the strategically modified hepatitis B protein near the desired insert region. The nucleotides of the restriction endonuclease site will be translated into amino acids upon expression, and that effect has some bearing on the choice of endonuclease. Several restriction endonucleases are commercially available (e.g. from Promega Corp., Madison, Wis.) and their recognition site sequences and cleavage sites well known in the art. Example 1 describes such a construct for a strategically modified hepatitis B core protein.

In one preferred embodiment, the insert is a single residue that is added as the chemically-reactive residue. In other preferred embodiments, the use of restriction enzymes and their recognition sequences causes about three to about five residues to be inserted, including the desired chemically reactive residue.

An insert containing a chemically-reactive amino acid residue is inserted into the native hepatitis B core protein at a position corresponding to an amino acid residue position from about 50 to about 100. The preferred region of insertion into the hepatitis B core protein is in the immunodominant loop region (about amino acid residue 70 to about 90), more preferably in the loop region that corresponds to the native hepatitis B core protein position from about amino acid 78 to about 82. Most preferably, the insert is placed at residues numbered 78 to 80 of SEQ ID NO:2.

As used herein when it is said that the insert is "at a position" it is meant that the amino terminus of the insert is peptide bonded to the carboxy terminus of the corresponding amino acid residue of the hepatitis B core protein sequence having that amino acid residue number. In other words, the insert immediately follows the residue at that stated position.

Insertion can be effected by generally utilized methods in the art. Genetic manipulation, by a PCR-based method is illustrated in Examples 1 and 5. In addition, oligonucleotide-mediated site directed mutagenesis as discussed in J. Sambrook et al. *Molecular Cloning: a laboratory manual,* $2^{nd}$ ed., Cold Spring Harbor Laboratory Press, 15.51-ff. (1989) can be used to add one codon by hybridizing a desired DNA sequence with a template that adds a codon for single residue, followed by filling in the remaining nucleic acid sequence. Dawson et al., Science 266:776–779 (1994), describe a method of linking polypeptide chains at their peptide backbone, so that a fusion could be built up of peptide fragments.

The chemically-reactive amino acid residue can be at any position within the insert. Preferably, the chemically-reactive amino acid residue is in a position that corresponds to amino acid residue numbered 70 to 90 of the native (wild type) core, and most preferably at residue position 78 to 82. For example, when a 10 amino acid residue long insert is inserted at a position corresponding to native core protein residue 73, then the chemically-reactive amino acid residue is preferably at position 5 to 9 of the insert. When a 30 amino acid residue long insert is inserted a position corresponding to native core protein residue 58, then the chemically-reactive amino acid residue is preferably at position 22 to 24 of the insert.

An introduced chemically-reactive amino acid residue has a chemically-reactive side chain that provides a functional group for derivatizing the strategically modified HBc (i.e. conjugating a hapten to the modified HBc). Useful side chain functional groups include epsilon-amino groups, beta- or gamma-carboxyl groups, thiol (-SH) groups and aromatic rings (e.g. tyrosine and histidine). The chemically-reactive amino acid residue is typically a lysine, cysteine, or histidine residue or a carboxyl-containing residue such as aspartic acid or glutamic acid. Lysine is a particularly preferred chemically-reactive amino acid residue.

It is noted that the amino acid residue sequence of the hepatitis B core protein encoded by and shown in SEQ ID NOs:1 and 2, respectively, has two consecutive endogenous carboxyl-containing residues, existing glutamic (glu, E) and aspartic (asp, D) acids, at positions 77 and 78. However, the present invention contemplates the introduction of at least one additional, exogenous chemically-reactive amino acid residue. European Patent No. 385610 reports that unsatisfactory results were achieved in attempts to chemically couple polypeptide haptens to HBc particles. It is noted that those coupling attempts were directed toward amino groups and not carboxyl groups of the amino acid side chains.

In addition of the use of an individual chemically-reactive amino acid residue in the insert such as aspartic acid or lysine, substantially any sequence of the desired length that contains a chemically-reactive amino acid residue can be used. Exemplary inserts of greater than a single residue include the B cell HRV-2 VP2 epitope discussed in B. E. Clarke et al. *Vaccines* 91:313–318 (1991), the HBsAg Pre-S(1)27–53 sequence discussed in F. Schödel et al. *J. Virol.* 66(1):106–114 (1992) and the HBsAg Pre-S(2)133–143 sequence discussed in F. Schödel et al. *Vaccines* 90:193–198 (1990). An appropriate T cell epitope discussed hereinafter as a hapten can also be used as an insert. Exemplary sequences include those of SEQ ID NOs: 28, 32, 33, 34, 47, 48, 49, 50 and 55.

ii. Additional Modification of the Core Protein

It is also contemplated that a hepatitis B core protein strategically modified as described above has other modifications. The contemplated modifications of the strategically modified core include the nature of the insert containing the chemically-reactive amino acid residue, truncation of the amino terminus, truncation of the carboxy terminus, fusion at the carboxy terminus, pendent linking to the carboxy-terminal region.

The insert containing the chemically-reactive amino acid residue to which the hapten is conjugated can have a use in addition to providing the chemically-reactive amino acid residue. It is contemplated that an insert containing a chemically-reactive amino acid residue is a T cell stimulating amino acid sequence. Such a T cell stimulating amino acid sequence is preferably a T cell epitope from the same source as the B cell epitope that will be the conjugated antigen, e.g. both from *Mycobacterium tuberculosis.* Exemplary epitopes are discussed hereinafter.

An insert containing a chemically-reactive amino acid residue can also be chosen in order to confer additional desirable properties, such as stability-enhancing or solubility-enhancing properties.

A strategically modified hepatitis B core protein can be chemically modified by methods well known in the art. Numerous such techniques are disclosed in Roger L.

Lundblad, *Techniques in Protein Modification*, CRC Press (Ann Arbor, Mich.: 1994). Such chemical modifications are made to enhance or diminish properties, for example, a lysine amino group can be blocked to change the isoelectric point of the protein, causing it to separate differently on a chromatographic ion exchange resin.

It is also contemplated that the carboxy terminus of the core protein sequence be truncated, preferably down to about amino acid residue position 140. The arginine-rich sequence present beginning at residue 150 of SEQ ID NO:2 binds to nucleic acids and can hinder the purification and handling of the expressed core protein. In SEQ ID NO:2, the arginine-rich stretches begin at position 150. A preferred strategically modified HBc protein has a carboxy terminal valine (V) residue of residue 149.

iii. Making Strategically-Modified Core Protein

The strategic modification of the hepatitis B core protein is typically made by known processes in the art on the DNA level, for example by inserting the codons corresponding to the amino acids to be inserted. The engineered gene is then expressed in a convenient system known in the art, for example in a viral culture in infected immortalized cells.

Methods for producing HBcAg proteins in general and the pre-core, core and HBeAg proteins in particular, are well known in the art. The same methods readily adapted to the isolation of the modified core protein particles of the invention. In addition, HBcAg and HBeAg can be produced by a variety of well known recombinant DNA techniques. See, for example, U.S. Pat. No. 4,356,270 to Itakura and U.S. Pat. No. 4,563,423 to Murray et al., respectively. Those recombinant DNA techniques can be easily adapted to produce modified core particles of the invention. The modified core proteins can be conjugated with hapten before or after particle formation, preferably after core particle formation and purification.

C. Modified Hepatitis B Core Protein Conjugate

Any hapten against which antibody production is desired can be linked to a strategically modified hepatitis B core protein to form an immunogenic strategically modified hepatitis B core protein conjugate of this invention. The hapten of interest typically is a B cell determinant. The hapten can be a polypeptide, a carbohydrate (saccharide), or a non-polypeptide, non-carbohydrate chemical such as 2,4-dinitrobenzene.

Methods for operatively linking individual haptens to a protein or polypeptide through an amino acid residue side chain of the protein or polypeptide to form a pendently-linked immunogenic conjugate, e.g., a branched-chain polypeptide polymer, are well known in the art. Those methods include linking through one or more types of functional groups on various side chains and result in the carrier protein polypeptide backbone being pendently linked—covalently linked (coupled) to the hapten but separated by at least one side chain.

Methods for linking carrier proteins to haptens using each of the above functional groups are described in Erlanger, *Method of Enzymology*, 70:85 (1980), Aurameas, et al., *Scand. J. Immunol.*, Vol. 8, Suppl. 7, 7–23 (1978) and U.S. Pat. No. 4,493,795 to Nestor et al. In addition, a site-directed coupling reaction, as described in Rodwell et al., *Biotech.*, 3, 889–894 (1985) can be carried out so that the biological activity of the polypeptides is not substantially diminished.

Furthermore, as is well known in the art, both the HBcAg protein and a polypeptide hapten can be used in their native form or their functional group content can be modified by succinylation of lysine residues or reaction with cysteine-thiolactone. A sulfhydryl group can also be incorporated into either carrier protein or conjugate by reaction of amino functions with 2-iminothiolane or the N-hydroxysuccinimide ester of 3-(3-dithiopyridyl) propionate.

The HBc protein or hapten can also be modified to incorporate a spacer arm, such as hexamethylene diamine or other bifunctional molecules of similar size, to facilitate the pendent linking.

Polypeptide hasten. Methods for covalent bonding of a polypeptide hapten are extremely varied and are well known by workers skilled in the immunological arts. For example, following U.S. Pat. No. 4,818,527, m-maleimidobenzoyl-N-hydroxysuccinimde ester (ICN Biochemicals, Inc.) or succinimidyl 4-(N-maleimidomethyl)cyclohexane-1-carboxylate (SMCC, Pierce) is reacted with a strategically modified hepatitis B core protein to form an activated carrier. That activated carrier is then reacted with a polypeptide that either contains a terminal cysteine or to which an additional amino- or carboxy-terminal cysteine residue has been added to form a covalently bonded strategically modified hepatitis B core protein conjugate. As an alternative example, the amino group of a polypeptide hapten can be first reacted with N-succinimidyl 3-(2-pyridylthio) propionate (SPDP, Pharmacia), and that thiol-containing polypeptide can be reacted with the activated carrier after reduction. Of course, the sulfur-containing moiety and double bond-containing Michael acceptor can be reversed. These reactions are described in the supplier's literature, and also in Kitagawa, et al., *J. Biochem.*, 79:233 (1976) and in Lachmann et al., in 1986 *Synthetic Peptides as Antigens*, (Ciba Foundation Symposium 119), pp. 25–40 (Wiley, Chichester: 1986).

U.S. Pat. No. 4,767,842 teaches several modes of covalent attachment between a carrier and polypeptide that are useful here. In one method, tolylene diisocyanate is reacted with the carrier in a dioxane-buffer solvent at zero degrees C to form an activated carrier. A polypeptide hapten is thereafter admixed and reacted with the activated carrier to form the covalently bonded strategically modified hepatitis B core protein conjugate.

Particularly useful are a large number of heterobifunctional agents that form a disulfide link at one functional group end and a peptide link at the other, including N-succidimidyl-3-(2-pyridyldithio) propionate (SPDP). This reagent creates a disulfide linkage between itself and a thiol in either the strategically modified hepatitis B core protein or the hapten, for example a cysteine residue in a polypeptide hapten, and an amide linkage on the coupling partner, for example the amino on a lysine or other free amino group in the carrier protein. A variety of such disulfide/amide forming agents are known. See for example *Immun. Rev.* (1982) 62:185. Other bifunctional coupling agents form a thioether rather than a disulfide linkage. Many of these thioether-forming agents are commercially available and include reactive esters of 6-maleimidocaproic acid, 2-bromoacetic acid, 2-iodoacetic acid, 4-(N-maleimidomethyl)cyclohexane-1-carboxylic acid and the like. The carboxyl groups can be activated by combining them with succinimide or 1-hydroxy-2-nitro-4-sulfonic acid, sodium salt. The particularly preferred coupling agent for the method of this invention is succinimidyl 4-(N-maleimidomethyl) cyclohexane-1-carboxylate (SMCC) obtained from Pierce Company, Rockford, Ill. The foregoing list is not meant to be exhaustive, and modifications of the named compounds can clearly be used, e.g., the sulpho-SMCC depicted in the figure.

A polypeptide hapten can be obtained in a number of ways well known in the art. Usual peptide synthesis techniques can be readily utilized. For example, recombinant and PCR-based techniques to produce longer peptides are useful. Because the desired sequences are usually relatively short, solid phase chemical synthesis is useful.

As discussed below, DNA sequences that encode a variety of polypeptide haptens are known in the art. The coding sequence for peptides of the length contemplated herein can easily be synthesized by chemical techniques, for example, the phosphotriester method of Matteucci et al., *J. Am. Chem. Soc.* 103:3185 (1981). Of course, by chemically synthesizing the coding sequence, any desired modification can be made simply by substituting the appropriate bases for those encoding the native peptide sequence. The coding sequence can then be provided with appropriate linkers and ligated into expression vectors now commonly available in the art, and the regulating vectors used to transform suitable hosts to produce the desired protein.

A number of such vectors and suitable host systems are now available. For example promoter sequences compatible with bacterial hosts are provided in plasmids containing convenient restriction sites for insertion of the desired coding sequence. Typical of such vector plasmids are, for example, pUC8, and pUC13 available from J. Messing, at the University of Minnesota (see, e.g., Messing et al., *Nucleic Acids Res.* 9:309 (1981)) or pBR322, available from New England Biolabs. Suitable promoters include, for example, the beta-lactamase (penicillinase) and lactose (lac) promoter systems (Chang. et al., *Nature* 198:1056 (1977) and the tryptophan (trp) promoter system (Goeddel et al., *Nucleic Acids Res.* 8:4057 (1980)). The resulting expression vectors are transformed into suitable bacterial hosts using the calcium chloride method described by Cohen, et al., *Proc. Natl. Acad. Sci. U.S.A.* 69:2110 (1972). Successful transformants may produce the desired polypeptide fragments at higher levels than those found in strains normally producing the intact pili. Of course, yeast or mammalian cell hosts can also be used, employing suitable vectors and control sequences.

TABLE 2

Polypeptide haptens

| Organism | Antigen | T or B cell epitope | Sequence | SEQ ID NO |
|---|---|---|---|---|
| *Streptococcus pneumoniae* | PspA | B | KLEELSDKIDELDAE | 25 |
| *Streptococcus pneumoniae* | PspA | B | SQKKYDEDQKKTEEKAALEKA ASEEMDKAVAAVQQA | 26 |
| *Cryptosporidium parvum* | P23 | B | QDKPADAPAAEAPAAEPAAQQ DKPADA | 27 |
| HIV | P24 | T | GPKEPFRDYVDRFYKC | 28 |
| HIV | GP120 | B | RKRIHIGPGRAFYITKN | 29 |
| Foot and Mouth Disease Virus | VP1 | B | YNGECRYNRNAVPNLRGDLQV LAQKVARTLP | 30 |
| *Corynebacterium diphtheriae* | toxin | T | FQVVHNSYNRPAYSPGC | 31 |
| *Borrelia burgdorferi* | OspA | T | VEIKEGTVTLKREIDKNGKVT VSLC | 32 |
| *Borrelia burgdorferi* | OspA | T | TLSKNISKSGEVSVELNDC | 33 |
| Influenza A8/PR8 | HA | T | SSVSSFERFEC | 34 |
| Influenza A8/PR8 | HA | B | YRNLLWLTEK | 35 |
| *Yersinia pestis* | V Ag | B | DILKVIVDSMNHHGDARSKLR EELAELTAELKIYSVIQAEIN KHLSSSGTINIHDKSINLMDK NLYGYTDEEIFKASAEYKILE KMPQTTIQVDGSEKKIVSIKD FLGSENKRTGALGNLKNSYSY NKDNNELSHFATTCSD | 36 |
| *Haemophilus influenzae* | pBOMP | B | CSSSNNDAAGNGAAQFGGY | 37 |
| *Haemophilus influenzae* | pBOMP | B | NKLGTVSYGEE | 38 |
| *Haemophilus influenzae* | pBOMP | B | NDEAAYSKNRRAVLAY | 39 |
| *Moraxella catarrhalis* | copB | B | LDIEKDKKKRTDEQLQAELDD KYAGKGY | 40 |
| *Moraxella catarrhalis* | copB | B | LDIEKNKKKRTEAELQAELDD KYAGKGY | 41 |
| *Moraxella catarrhalis* | copB | B | IDIEKKGKIRTEAELLAELNK DYPGQGY | 42 |
| *Porphyromonas gingivalis* | HA | B | GVSPKVCKDVTVEGSNEFAPV QNLT | 43 |
| *Porphyromonas gingivalis* | HA | B | RIQSTWRQKTVDLPAGTKYV | 44 |
| *Trypanosoma cruzi* | | T | SHNFTLVASVIIEEAPSGNTC | 45 |
| *Trypanosoma cruzi* | | B | KAAIAPAKAAAAPAKAATAPA | 46 |
| *Plasmodium falciparum* | MSP1 | T | SVQIPKVPYPNGIVYC | 47 |
| *Plasmodium* | MSP1 | T | DFNHYYTLKTGLEADC | 48 |

TABLE 2-continued

Polypeptide haptens

| Organism | Antigen | T or B cell epitope | Sequence | SEQ ID NO |
|---|---|---|---|---|
| *falciparum* | | | | |
| *Streptococcus sobrinus* | AgI/II | B & T | KPRPIYEAKLAQNQKC | 49 |
| *Streptococcus sobrinus* | AgI/II | B & T | AKADYEAKLAQYEKDLC | 50 |
| lymphocytic Choriomeningitis virus | NP | T | RPQASGVYMGNLTAQC | 51 |
| *Shigella flexneri* | Invasin | B | KDRTLIEQK | 52 |
| respiratory synctial virus | G | B | CSICSNNPTCWAICK | 53 |
| *Plasmodium vivax* | CS | B | GDRADGQPAGDRADGQPAG | 54 |
| *Clostridium tetani* | tox | T | QYIKANSKFIGITELC | 55 |
| *Entamoeba histolytica* | lectin | B | VECASTVCQNDNSCPIIADVEKCNQ | 56 |
| *Schistosoma japonicum* | para | B | DLQSEISLSLENGELIRRAKSAESLASELQRRVD | 57 |
| *Schistosoma mansoni* | para | B | DLQSEISLSLENSELIRRAKAAESLASDLQRRVD | 58 |
| *Plasmodium vivax* | | B | DRAAGQPAGDRADGQPAG | 83 |
| Influenza virus | Infl | B | CNNPHRIL | 84 |
| Influenza virus | Infl | T | CPKYVKQNTLKLATGMRNVPEKQTR | 85 |
| Influenza virus | Infl | B | SIMRSDAPIGTCSSECITPNGSIPNDKPFQNVNKITY | 14 |
| Influenza virus | Infl | B | RGIFGAIAGFIENGWEGMIDGWYGFRHQN | 15 |
| Influenza virus | Infl | B | EKQTRGIFGA | 16 |
| *Mycobacterium tuberculosis* | | T | AVLEDPYILLVSSKV | 86 |
| *Mycobacterium tuberculosis* | | T | LLVSSKVSTVKDLLP | 87 |
| *Mycobacterium tuberculosis* | | T | LLPLLEKVIGAGKPL | 88 |
| *Mycobacterium tuberculosis* | | T | AILTGGQVISEEVGL | 89 |
| *Mycobacterium tuberculosis* | | T | IAFNSGLEPGVVAEK | 90 |
| *Mycobacterium tuberculosis* | | T | ARRGLERGLNALADAVKV | 91 |
| *Mycobacterium tuberculosis* | | T | EKIGAELVKEVAKK | 92 |
| *Mycobacterium tuberculosis* | | T | GLKRGIEKAVEKVTETL | 93 |
| *Mycobacterium tuberculosis* | | T | IEDAVRNAKAAVEEG | 94 |
| Feline leukemia virus | FeLV | B | CDIIGNTWNPSDQEPFPGYG | 95 |
| Feline leukemia virus | FeLV | B | CIGTVPKTHQALCNETQQGHT | 96 |
| Feline leukemia virus | FeLV | B | GNYSNQTNPPPSC | 97 |
| Feline leukemia virus | FeLV | B | TDIQALEESISALEKSLTSLSE | 98 |
| Feline leukemia virus | FeLV | | AKLRERLKQRQQLF | 99 |
| Feline leukemia virus | FeLV | | DSQQGWFEGWFNKSPWFTTLISS | 100 |
| Feline leukemia virus | FeLV | | QVMTITPPQAMGPNLVLP | 101 |
| Feline leukemia virus | FeLV | | DQKPPSRQSQIESRVTP | 102 |
| Feline leukemia virus | FeLV | | RRGLDILFLQEGGLC | 103 |
| Feline leukemia virus | FeLV | | QEGGLCAALEECQIGGLCAALKEEC | 104 |
| *Plasmodium falciparum* | | B | NANPNANPNANP | 105 |
| Circumsporozoite | | | QAQGDGANAGQP | 113 |

Chemical Hapten. Related chemistry is used to couple chemical compounds to carrier proteins. Typically, an appropriate functional group for coupling is designed into the chemical compound.

Antibodies to the compound 6-O-phosphocholine hydroxyhexanoate protect against *Streptococcus pneumoniae*. Randy T. Fischer et al. *J. Immunol.*, 154:3373–3382 (1995).

TABLE 3

Chemical Haptens

| Chemical Hapten | Citation |
| --- | --- |
| piperidine N-oxide | U.S. Pat. No. 5,304,252 |
| phospholactone or lactamide | U.S. Pat. No. 5,248,611 |
| metal ion complexes [2.2.1] or [7.2.2] bicyclic ring compounds | U.S. Pat. No. 5,236,825 U.S. Pat. No. 5,208,152 |
| ionically charged hydroxyl - containing compounds | U.S. Pat. No. 5,187,086 |
| phosphonate analogs of carboxylate esters | U.S. Pat. No. 5,126,258 |
| cocaine analogs | Carrera et al., Nature 378:725 (1995) |

Carbohydrate Hapten. There are many methods known in the art to couple carrier proteins to polysaccharides. Aldehyde groups can be generated on either the reducing end [Anderson, *Infect. Immun.*, 39:233–238 (1983); Jennings, et al., *J. Immunol.*, 127:1011–1018 (1981); Poren et al., Mol. Immunol., 22:907–919 (1985)] or the terminal end [Anderson et al., *J. Immunol.*, 137:1181–1186 (1986); Beuvery et al., *Dev. Bio. Scand.*, 65:197–204 (1986)] of an oligosaccharide or relatively small polysaccharide, which can be linked to the carrier protein via reductive amination.

Large polysaccharides can be conjugated by either terminal activation [Anderson et al., *J. Immunol.*, 137:1181–1186 (1986)] or by random activation of several functional groups along the polysaccharide chain [Chu et al., *Infect. Immun.*, 40:245–256 (1983); Gordon, U.S. Pat. No. 4,619,828 (1986); Marburg, U.S. Pat. No. 4,882,317 (1989)]. Random activation of several functional groups along the polysaccharide chain can lead to a conjugate that is highly cross-linked due to random linkages along the polysaccharide chain. The optimal ratio of polysaccharide to carrier protein depend on the particular polysaccharide, the carrier protein, and the conjugate used.

See Dick et al., in *Contributions to Microbiology and Immunology*, Vol. 10, Cruse et al., eds., (S. Karger: 1989), pp. 48–114; Jennings et al., in *Neoglycoconjugates: Preparation and Applications*, Lee et al., eds., (Academic Press: 1994), pp. 325–371; Aplin et al., *CRC Crit. Rev. Biochem.*, 10:259–306 (1981); and Stowell et al., *Adv. Carbohydr. Chem. Biochem.*, 37:225–281 (1980) for detailed reviews of methods of conjugation of saccharide to carrier proteins.

The carbohydrate itself can be synthesized by methods known in the art, for example by enzymatic glycoprotein synthesis as described by Witte et al., *J. Am. Chem. Soc.*, 119:2114–2118 (1997).

Several oligosaccharides, synthetic and semi-synthetic, and natural, are discussed in the following paragraphs as examples of oligosaccharides that are contemplated haptens to be used in making a strategically modified core protein conjugate of the present invention.

An oligosaccharide hapten suitable for preparing vaccines for the treatment of Haemophilus Influenza type b (Hib) is made up of from 2 to 20 repeats of D-ribose-D-ribitol-phosphate (I, below), D-ribitol-phosphate-D-ribose (II, below), or phosphate-D-ribose-D-ribitol (III, below). Eduard C. Beuvery et al., EP-0 276 516-B1.

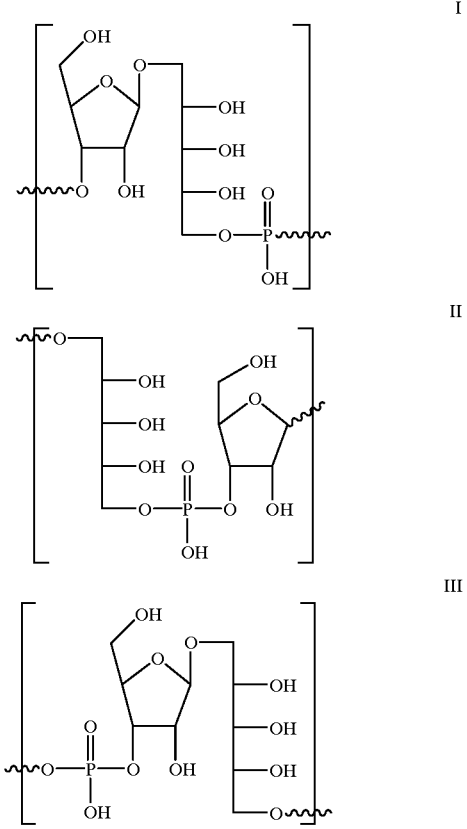

U.S. Pat. No. 4,220,717 also discloses a polyribosyl ribitol phosphate (PRP) hapten for *Haemophilus influenzae* type b.

Ellena M. Peterson et al., *Infection and Immunity*, 66(8):3848–3855 (1998), disclose a trisaccharide hapten, αKdo(2 8)αKdo(2 4)αKdo, that provides protection from *Chlamydia pneumoniae*. *Chlamydia pneumoniae* is a cause of human respiratory infections ranging from pharyngitis to fatal pneumonia. Kdo is 3-deoxy-D-manno-oct-2-ulosonic acid.

Bengt Andersson et al., EP-0 126 043-A1, disclose saccharides that can be used in the treatment, prophylaxis or diagnosis of bacterial infections caused by *Streptococci pneumoniae*. One class of useful saccharides are derived from the disaccharide GlcNAcβ1 3 Gal. Andersson et al. also found neolactotetraosylceramide to be useful, which is Galβ1 4GlcNAcβ1 3Galβ1 4Glc-Cer.

European Patent No. 0 157 899-B1, the disclosures of which are incorporated herein by reference, discloses the isolation of pneumococcal polysaccharides that are useful in the present invention. The following table lists the pneumococcal culture types that produce capsular polysaccharides useful as haptens in the present invention.

TABLE 4

Polysaccharide Hapten Sources

| Danish Type Nomenclature | U.S. Nomenclature | 1978 ATCC Catalogue Number |
|---|---|---|
| 1 | 1 | 6301 |
| 2 | 2 | 6302 |
| 3 | 3 | 6303 |
| 4 | 4 | 6304 |
| 5 | 5 | |
| 6A | 6 | 6306 |
| 6B | 26 | 6326 |
| 7F | 51 | 10351 |
| 8 | 8 | 6308 |
| 9N | 9 | 6309 |
| 9V | 68 | |
| 10A | 34 | |
| 11A | 43 | |
| 12F | 12 | 6312 |
| 14 | 14 | 6314 |
| 15B | 54 | |
| 17F | 17 | |
| 18C | 56 | 10356 |
| 19A | 57 | |
| 19F | 19 | 6319 |
| 20 | 20 | 6320 |
| 22F | 22 | |
| 23F | 23 | 6323 |
| 25 | 25 | 6325 |
| 33F | 70 | |

*Moraxella* (Branhamella) *catarrhalis* is a know cause of otitis media and sinusitis in children and lower respiratory tract infections in adults. The lipid A portion of the lipoo-ligosaccharide surface antigen (LOS) of the bacterium is cleaved at the 3-deoxy-D-manno-octulosonic acid-glucosamine linkage. The cleavage product is treated with mild-alkali to remove ester-linked fatty acids while preserving amide-linked fatty acids to yield detoxified lipopolysaccharide (dLOS) from M. catarrhalis. The dLOS is not immunogenic until it is attached to a protein carrier. Xin-Xing Gu, et al. *Infection and Immunity* 66(5):1891–1897 (1998).

Group B streptococci (GBS) is a cause of sepsis, meningitis, and related neurologic disorders in humans. The Capsular polysaccharide-specific antibodies are known to protect human infants from infection. Jennings et al., U.S. Pat. No. 5,795,580. The repeating unit of the GBS capsular polysaccharide type II is: 4)-β-D-GlcpNAc-(1 3)-[β-D-Galp(1 6)]-β-D-Galp(1 4)-β-D-Glcp-(1 3)-β-D-Glcp-(1 2)-[α-D-NeupNAc(2 3)]-β-D-Galp-(1, where the bracketed portion is a branch connected to the immediately following unbracketed subunit. The repeating unit of GBS capsular polysaccharide type V is: 4)-[α-D-NeupNAc-(2 3)-β-D-Galp-(1 4)-β-D-GlcpNAc-(1 6)]-α-D-Glcp-(1 4)-[β-D-Glcp-(1 3)]-β-D-Galp-(1 4)-β-D-Glcp-(1.

European patent application No. EU-0 641 568-A1, Dr. Helmut Brade, discloses the method of obtaining ladder-like banding pattern antigen from *Chlamydia trachomatis, pneumoniae* and *psittaci.*

D. Pathogen-related Conjugate to the Modified HBc

In one embodiment of the invention, the hapten that is conjugated to strategically modified HBc protein is a B cell determinant of a pathogen. B cell determinants of numerous pathogens are known in the art, and several were illustrated in the preceding discussions of polypeptide and carbohydrate haptens.

In preferred embodiments, the hapten is a pathogen-related hapten. The use of a portion of a pathogen's protein sequence or carbohydrate sequence as a hapten has distinct advantages over the exposure to an actual pathogen, and even over a passivated or "killed" version of the pathogen.

Exemplary pathogen-related haptens of particular importance are derived from bacteria such as *B. pertussis, S. typosa, S. paratyphoid* A and B, *C. diptheriae, C. tetani, C. botulinum, C. perfringens, B. anthracis, P. pestis, P. multocida, V. cholerae, N. meningitides, N. gonorrhea, H. influenzae, T. palladium,* and the like.

Other exemplary sources of pathogen-related haptens of particular importance are viruses such as poliovirus, adenovirus, parainfluenza virus, measles, mumps, respiratory syncytial virus, influenza virus, equine encephalomyelitis virus, hog cholera virus, Newcastle virus, fowl pox virus, rabies virus, feline and canine distemper viruses, foot and mouth disease virus (FMDV), human and simian immunodeficiency viruses, and the like. Other important sources of pathogen-related haptens include rickettsiae, epidemic and endemic typhus, the spotted fever groups, and the like.

Pathogen-related polypeptide haptens are well-known in art and are discussed in numerous disclosures such as U.S. Pat. Nos. 3,149,036, 3,983,228, and 4,069,313; in *Essential Immunology,* 3$^{rd}$ Ed., by Roit, published by Blackwell Scientific Publications; in *Fundamentals of Clinical Immunology,* by Alexander and Good, published by W. B. Saunders; and in *Immunology,* by Bellanti, published by W. B. Saunders.

Particularly preferred pathogen-related haptens are those described in U.S. Pat. Nos. 4,625,015, 4,544,500, 4,545,931, 4,663,436, 4,631,191, 4,629,783 and in Patent Cooperation Treaty International Publication No. WO87/02775 and No. WO87/02892, all of whose disclosures are incorporated herein by reference.

Antibodies that immunoreact with the hepatitis B virus can be obtained by using modified HBc conjugated with a polypeptide hapten that corresponds to the sequence of a determinant portion of HBsAg; in particular, residues 110–137 of the "S" (surface) region disclosed in Gerin et al., *Proc. Natl. Acad. Sci. USA,* 80:2365 (1983).

Another conjugate corresponds to amino acids 93–103 of capsid protein VPI of poliovirus type 1 (PV1, Mahoney strain), analogous to the work by Delpeyroux et al., *Science,* 233:472–475 (1986). Such a modified HBc conjugate provides antibodies that immunoreact with polio. Other potential haptens from poliovirus type 1, Mahoney and Sabin strains are described in European Patent No. 385610.

In preferred embodiments, the hapten is a pathogen-related hapten that immunoreacts with; i.e., is immunologically bound by, antibodies induced by the pathogen. More preferably, the pathogen-related hapten induces an antibody response that provides protection against infection by the pathogen.

Methods for determining the presence of antibodies to an immunogen in a body sample from an immunized animal are well known in the art. Methods for determining the presence of both cross-reactive and protective antibodies are well known in the art.

In another embodiment of the invention, the immune response to the B cell determinant is boosted by also providing a T cell determinant.

For example, U.S. Pat. No. 4,882,145 describes T cell stimulating polypeptides derived from the HBV nucleocapsid protein. Other T cell determinants are known in the art and can be used as an operatively linked determinant in a contemplated modified HBc protein or particle.

In a particularly preferred embodiment of the invention, such a T cell determinant is derived from the same pathogen as the B cell determinant that is conjugated to the modified HBc. The T cell determinants of various pathogens are reported in the art.

Although it is preferred that the B and T cell determinants are derived from the same pathogen, it is not necessary that they be from the same protein of that pathogen. For example, the B cell determinant from the VP1 protein of the foot and mouth disease virus (FMDV) can be conjugated to a modified HBc particle, wherein the HBc protein is further modified by having a T cell determinant derived from the VP4 protein of FMDV.

The additional T cell determinant can be introduced into a modified HBc protein on the genetic level using well-known methods within or at a terminus of the HBc protein sequence (amino or carboxy termini), including as part of the DNA inserted to introduce the chemically-reactive amino acid residue, but preferably as a fusion protein at the carboxy terminus. Alternatively, the additional T cell determinant can be operatively linked to the conjugated B cell determinant or the strategically modified HBc protein.

Exemplary disclosures that describe techniques for genetically engineering a DNA sequence that can be used to produce a fusion protein of the present invention can be found in: U.S. Pat. No. 4,428,941 to Galibert et al., U.S. Pat. No. 4,237,224 to Cohen et al.: U.S. Pat. No. 4,273,875 to Manis; U.S. Pat. No. 4,431,739 to Riggs; U.S. Pat. No. 4,363,877 to Goodman et al., and Rodriguez & Tait, *Recombinant DNA Techniques: An Introduction,* The Benjamin-Cummings Publishing Co., Inc. Menlo Park, Calif. (1983), whose disclosures are incorporated by reference.

E. Inocula and Vaccines

In yet another embodiment of the invention, a modified HBc protein or particle conjugated to a hapten (a HBc conjugate) is used as the immonogen of an inoculum that induces production of antibodies that immunoreact with the hapten or as a vaccine to provide protection against the pathogen from which the hapten is derived.

A contemplated inoculum or vaccine comprises a HBcAg conjugate that is dissolved or dispersed in a pharmaceutically acceptable diluent composition that typically also contains water. When administered in an immunogenic effective amount to an animal such as a mammal (e.g., a mouse, dog, goat, sheep, horse, bovine, monkey, ape, or human) or bird (e.g., a chicken, turkey, duck or goose), an inoculum induces antibodies that immunoreact with the conjugated (pendently-linked) hapten. A vaccine is a type of inoculum in which the hapten is pathogen related and the induced antibodies not only immunoreact with the hapten, but also immunoreact with the pathogen or diseased cell, and neutralize the pathogen or diseased cell with which they immunoreact.

The preparation of inocula and vaccines that contain proteinaceous materials as active ingredients is also well understood in the art. Typically, such inocula or vaccines are prepared as parenterals, either as liquid solutions or suspensions; solid forms suitable for solution in, or suspension in, liquid prior to injection can also be prepared. The preparation can also be emulsified. The immunogenic active ingredient is often mixed with excipients that are pharmaceutically acceptable and compatible with the active ingredient. Suitable excipients are, for example, water, saline, dextrose, glycerol, ethanol, or the like and combinations thereof. In addition, if desired, an inoculum or vaccine can contain minor amounts of auxiliary substances such as wetting or emulsifying agents, pH buffering agents or adjuvants which enhance the immunogenic effectiveness of the composition.

Exemplary adjuvants include complete Freund's adjuvant (CFA) that is not used in humans, incomplete Freund's adjuvant (IFA) and alum, which are materials well known in the art, and are available commercially from several sources. The use of small molecule adjuvants is also contemplated herein.

Exemplary of one group of small molecule adjuvants are the so-called muramyl dipeptide analogues described in U.S. Pat. No. 4,767,842. Another type of small molecule adjuvant described in U.S. Pat. No. 4,787,482 that is also useful herein is a 4:1 by volume mixture of squalene or squalane and Aracel™ A (mannide monooleate).

Yet another type of small molecule adjuvant useful herein is a 7-substituted-8-oxo or 8-sulfo-guanosine derivative described in U.S. Pat. Nos. 4,539,205, 4,643,992, 5,011,828 and 5,093,318, whose disclosures are incorporated by reference. of these materials, 7-allyl-8-oxoguanosine (loxoribine) is particularly preferred. That molecule has been shown to be particularly effective in inducing an antigen-(immunogen-)specific response Inocula and vaccines are conventionally administered parenterally, by injection, for example, either subcutaneously or intramuscularly. Additional formulations that are suitable for other modes of administration include suppositories and, in some cases, oral formulation or by nasal spray. For suppositories, traditional binders and carriers can include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like.

An inoculum or vaccine composition takes the form of a solution, suspension, tablet, pill, capsule, sustained release formulation or powder, and contains an immunogenic amount of strategically modified HBc protein conjugate or strategically modified HBc protein particle conjugate as active ingredient. In a typical composition, an immunogenic amount of strategically modified HBc protein conjugate or strategically modified HBc protein particle conjugate is about 50 μg to about 2 mg of active ingredient per dose, and more preferably about 100 μg to about 1 mg per dose.

The particles and protein conjugates can be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived form inorganic bases such as, for example, sodium, potassium, ammonium, calcium, or ferric hydroxides, and such organic bases as isopropylamine, trimethylamine, 2-ethylamino ethanol, histidine, procaine, and the like.

The inocula or vaccines are administered in a manner compatible with the dosage formulation, and in such amount as are therapeutically effective and immunogenic. The quantity to be administered depends on the subject to be treated, capacity of the subject's immune system to synthesize antibodies, and degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in intervals (weeks or months) by a subsequent injection or other administration.

Another embodiment of the invention is a process for inducing antibodies in an animal host comprising the steps of inoculating said animal host with an inoculum. The inoculum used in the process comprises an immunogenic amount of a strategically modified hepatitis B core protein conjugate dissolved or dispersed in a pharmaceutically acceptable diluent. The strategically modified hepatitis B core protein conjugate used in the process comprises a hapten pendently linked to a strategically modified hepatitis B core protein. Preferably the strategically modified hepatitis B core protein is in particle form. The strategically modified hepatitis B core protein comprises an amino acid sequence corresponding to the hepatitis B core protein amino acid sequence of SEQ ID NO:2 including the amino acid residues numbered about 10 to about 140 and additionally having an insert in the region corresponding to amino acid residues numbered about 50 to about 100, said insert (i) being 1 to about 40 amino acid residues in length, and (ii) containing a chemically-reactive amino acid residue. The hapten is pendently linked to the strategically modified hepatitis B core protein through said chemically-reactive amino acid residue. Preferably, the hapten is pathogen-related. The animal is maintained for a time sufficient for antibodies to be induced.

The invention is illustrated by the following non-limiting examples.

EXAMPLE 1

Construction of a Modified Hepatitis B Core Protein Expression Vector

Using site-directed mutagenesis, a lysine codon (TTT) was introduced between amino acids D78 and P79 of the HBc gene, along with EcoRI (GAATTC) and SacI (GAGCTC) restriction endonuclease sites to facilitate the genetic insertion of other condons for producing strategically modified hybrid HBc particles. The insert thus had an amino acid residue sequence GIQKEL, where the GIQ is an artifact of the EcoRI site and the EL is an artifact of the SacI site. The strategically modified hepatitis B core protein was therefore 155 amino acid residues long. The construction of the pKK322-HBc155-K81 expression plasmid is described below.

Oligonucleotide primers P1F (SEQ ID NO:17) and P1R (SEQ ID NO:18, on the complementary strand) were used to amplify the 5' end of the HBc gene (bases 1–234, amino acids 1–78), and simultaneously incorporate an NcoI restriction site (CCATGG) at the 5' end, and an EcoRI restriction site (GAATTC) at the 3' end of the amplified product. Oligonucleotide primers (SEQ ID NO:19) P2F and P2R (SEQ ID NO:20, on the complementary strand) were used to amplify the 3' end of the HBc gene (bases 232–450, amino acids 79–149), and simultaneously incorporate an EcoRI restriction site (GAATTC) at the 5' end, a SacI restriction site (GAGCTC) adjacent to it, an inserted lysine codon (AAA) between them, and a HindIII restriction site at (AAGCTT) the 3' end of the amplified product.

The two PCR products (encoding amino acids 1–78 and amino acids 79–149) were cleaved with EcoRI, ligated together at their common EcoRI overhangs, cleaved with NcoI and HindIII and cloned into the expression plasmid pKK332 (Pharmacia), using standard techniques. The resulting plasmid was called pKK332-HBc-K81. This plasmid can be used for the expression of a strategically modified HBc protein bearing a lysine in the immunodominant loop. The expressed strategically modified HBc protein spontaneously formed particles. The strategically modified HBc of this Example thus had an insert corresponding to position 78 of the HBc of SEQ ID NO:2, a chemically reactive lysine residue at a position corresponding to position 82 of the HBc of SEQ ID NO:2, and was truncated at a position corresponding to position 149 of the HBc of SEQ ID NO:2.

EXAMPLE 2

Modified Hepatitis B Core Particle Purification

Strategically modified HBc particles of Example 1 were expressed in $E.\ coli$ typically $E.\ coli$ BLR or BL21 from Novagen (Madison, Wis.) or $E.\ coli$ TB11 from Amersham (Arlington Heights, Ill.). The transfected $E.\ coli$ denoted HBc155-K81, were expressed plasmid pKK332-HBc155-K81. The strategically modified HBc particles were purified via Sepharose CL-4B chromatography using established procedures. Because particles purify in a predictable manner, the monitoring of particle elution using simple spectroscopy ($OD_{280}$), in concert with SDS-PAGE analysis to assess purity of individual fractions prior to pooling, was sufficient to enable the routine purification of electrophoretically pure particles in high yield (5–120 mg/L cell culture). The spherical structure of the pure strategically modified hepatitis B core particles was clearly visible in an electron micrograph.

EXAMPLE 3

Chemical Coupling of Synthetic Peptides and Modified Hepatitis B Core Particles

The strategically modified heptatitis B core particle product of the expression plasmid pKK332-HBc155-K81 from Example 1 was assayed for its chemical reactivity compared with similarly expressed and purified "wild type" truncated hepatitis B core particle HBc149, which is identical to HBc155-K81 except that it lacks the introduced lysine residue and flanking five amino acids.

Synthetic peptides (haptens) were chemically conjugated to HBc particles using succinimidyl 4-(N-maleimido-methyl) cyclohexane 1-carboxylate (SMCC), a water-soluble heterobifunctional cross-linking reagent. SMCC is reactive towards both sulfhydryl and primary amino groups, enabling the sequential conjugation of synthetic peptides to HBc particles whose primary amino groups have previously been modified with SMCC. Further, the 11.6 angstrom spacer arm afforded by SMCC helps to reduce steric hindrance between the hapten and the HBc carrier, thereby enabling higher coupling efficiencies.

Briefly, HBc155-K81 and HBc149 particles were separately reacted with a 3-fold excess of SMCC over total amino groups (native amino groups or native amino groups plus the one from the lysine residue of the insert) for 2 hours at room temperature in 50 AM sodium phosphate, pH 7.5, to form maleimide-activated HBc particles. Unreacted SMCC was removed by repeated dialysis against 50 mM sodium phosphate, pH 7.0. The SMCC derivatization of the HBc particles resulted in a minimal molecular weight increase which was not detectable by SDS-PAGE. However, the PAGE analysis did confirm the integrity of the HBc proteins prior to proceeding to the peptide conjugation step.

Synthetic peptides to be coupled to the HBc particles were designed such that they had N-terminal cysteine residues to enable directional conjugation of peptide haptens to the primary amine on the side chain of the introduced lysine residue via the cysteine sulfhydryl of the hapten.

Table 2 shows the synthetic peptides derived from human cytochrome P450 enzymes that were chemically conjugated to HBc particles. The synthetic peptides were dissolved in 50 mM sodium phosphate, pH 7.0, to a concentration of 10 mg/ml. The synthetic peptides were then added, dropwise, to a 5-fold excess over total amino groups in maleimide-activated strategically modified HBc155-K81 particles, and permitted to react at room temperature for 2 hours. Maleimide-activated HBc149 particles were reacted with the two 2D6 peptides (206 and 206-C)as controls.

TABLE 5

Cytochrome P-450 Haptens

| Peptide Name | Sequence | SEQ ID NO.: |
|---|---|---|
| 1A1 (289–302) | CQEKQLDENANVQL | 21 |
| 1A2 (291–302) | CSKKGPRASGNLI | 22 |
| 2D6 (263–277) | CLTEHRMTWDPAQPPRDLT | 23 |
| 3A4 (253–273) | CVKRMKESRLEDTQKHRVDFLQ | 24 |
| 1A1-c | CMQLRS | 106 |
| 1A2-c | CRFSIN | 107 |
| 2D6-c | CAVPR | 108 |
| 2E1-c | CIPRS | 109 |
| 2C-c | CFIPV | 110 |
| 3A3/4/7-c | CTVSGA | 111 |
| 3A5-c | CTLSGE | 112 |

EXAMPLE 4

Analysis of Modified Core Particles Conjugates

Strategically modified HBc particles pendently linked to cytochrome P-450 determinant haptens of Example 3 were analyzed by SDS-PAGE and immunoblots to determine if synthetic peptides had been successfully conjugated to HBc. The denaturing conditions of the electrophoresis dissemble of particles into their constituent subunits, HBc monomers. Because HBc monomers have a molecular weight of approximately 16,000 Da, it was simple to resolve HBc155-K81 particles chemically conjugated to either 1A1 (289–302), 1A2 (291–302), 2D6 (263–277) or 3A4 (253–273) peptides, as those peptides have a relative molecular mass of approximately 2,000 Da and therefore cause a visible increase in the molecular mass of the HBc protein monomers. From the relative intensities of the conjugated and non-conjugated bands on SDS-PAGE, it was revealed that approximately 50 percent of the HBc155-K81 monomers were operatively linked to hapten, whereas only about 5 percent of the "wild type" HBc149 particles were linked to hapten. The marked increase in the observed success in pendently linking hapten to the strategically modified hepatitis B core protein supports the conclusion that the observed linking occurs via the inserted lysine as opposed to a lysine residue that is also present in the "wild type."

The shift in mobility of HBc particles conjugated to shorter C-terminal P450 derived peptides (5 and 6-mers) is not as pronounced in the SDS-PAGE as that of the longer inhibitory peptides, but shifts of approximately 700 Da were clearly evident in successfully coupled HBc155-K81 monomers. The strategically modified HBc 155-K81 protein exhibited markedly enhanced ability to pendently link to a hapten over the "wild type" HBc149 particles, which showed minimal conjugation.

In the model of core particles propounded by Conway et al. of icosahedral particles of either 180 or 240 associated core protein monomers [*Nature,* 386:91–94 (1997)], dimers of the relatively exposed immunodominant loop regions of the core monomers extend out from the assembled core particle into solution like spikes on a mace. The "spikes" are closely arranged spatially on the HBc particles. The strategic location of the introduced lysine residue on the tip of the spike minimizes the propensity for steric constraints to reactions to link haptens to the assembled core particle. A maximum of 50 percent of the strategically modified HBc monomers were successfully conjugated to the synthetic peptides of Cyt P-450. That amount of pendent linkage corresponds to an average of one hapten attached per core particle spike. This proposed distribution of hapten linkage to the strategically modified HBc particle is supported by PAGE results under semi-denaturing conditions that dissemble the particle while maintaining the dimer association.

HBc-2D6 particles, prepared by peptide coupling, were examined using immunoblots to confirm the presentation of the 2D6 epitope. When probed with anti-HBc antisera, the chemically coupled particle yielded two different monomers representing particles with and without the 2D6 peptide. only the upper band of which blotted with anti-2D6 antisera, thereby confirming the correlation between mobility shift and attachment of the 2D6 peptide.

EXAMPLE 6

Strategic Lysine Insertions

To construct HBc particles with inserted lysine residues at every position in the immunodominant, surface-exposed loop region (amino acids 75–85), PCR was used to amplify the 5' and 3' fragments of the HBc gene and a single lysine codon was introduced via the oligonucleotide primers. The oligonucleotide primers and the resulting amino acid sequences are shown in SEQ ID NOs: 61–82. The "wild type" sequences are SEQ ID NOs:59–60.

In order to generate lysine inserts at positions 75 to 84 (HBc-K75 through HBc-K84), the pairs of PCR fragments were digested with the restriction endonuclease MseI, which recognizes the sequence, AATT. The modified gene was restored by ligating the oligonucleotide primer (containing the lysine) at the convenient MseI restriction site located at nucleotides 221–224. For HBc-K85 (SEQ ID NOs:85–86) it was necessary to generate two fragments that were ligated at a common XhoI restriction site (CTCGAG) that is not present in the wild type gene, but could be introduced at position 239–244 without altering any amino acids.

TABLE 6

Lysine insertion mutants of HBc in the immunodominant loop

| Name | Sequence | SEQ ID NO: |
|---|---|---|
| Wild Type HBc | TWVGVNLEDPASRDLVVSYV | 60 |
| K75 | TWVGVKNLEDPASRDLVVSYV | 62 |
| K76 | TWVGVNKLEDPASRDLVVSYV | 64 |
| K77 | TWVGVNLKEDPASRDLVVSYV | 66 |
| K78 | TWVGVNLEKDPASRDLVVSYV | 68 |
| K79 | TWVGVNLEDKPASRDLVVSYV | 70 |
| K80 | TWVGVNLEDPKASRDLVVSYV | 72 |
| K81 | TWVGVNLEDPAKSRDLVVSYV | 74 |
| K82 | TWVGVNLEDPASKRDLVVSYV | 76 |
| K83 | TWVGVNLEDPASRKDLVVSYV | 78 |
| K84 | TWVGVNLEDPASRDKLVVSYV | 80 |
| K85 | TWVGVNLEDPASRDLKVVSYV | 82 |

To purify the strategically modified HBc proteins, cleared cell lysates from a 1L fermentation were precipitated with 45% ammonium sulfate and the resultant pellet subjected to gel filtration using Sepharose CL-4B chromatography (2.5cm×100cm). Particulate HBc has a characteristic elution position when analyzed using this type of column, which was independent of the amino acid insertions made to the particle. The eleven strategically modified HBc particles generated for this study were analyzed using this procedure, and the elution profiles were measured spectrophotometrically at an absorbance of 280 nm.

Three of the constructs (HBc-K75, HBc-K77, and HBc-K79) were produced at levels of between 50 and 100 mg/L, which is comparable with typical yields for wild-type, unmodified HBc particles, e.g. HBc149 particles. Four of the constructs (HBc-K76, HBc-K78, HBc-K81, and HBc-K82) were produced at relatively low levels of between 1 and 20 mg/L. Finally, four of the particles (HBc-K80, HBc-K83, HBc-K84, and HBc-K85) were produced at levels deemed to be barely detectable (<1 mg/L).

TABLE 7

Yields of purified lysine-containing HBc particles from a 1L fermentation

| Particle | Yield (mg/L) |
|---|---|
| HBc-150 (K75) | 77 |
| HBc-150 (K76) | 5 |
| HBc-150 (K77) | 74 |

TABLE 7-continued

Yields of purified lysine-containing HBc particles from a 1L fermentation

| Particle | Yield (mg/L) |
|---|---|
| HBc-150 (K78) | 10 |
| HBc-150 (K79) | 94 |
| HBc-150 (K80) | 0 |
| HBc-150 (K81) | 17 |
| HBc-150 (K82) | 1 |
| HBc-150 (K83) | 0 |
| HBc-150 (K84) | 0 |
| HBc-150 (K85) | 0 |

The foregoing description of the invention, including the specific embodiments and examples, is intended to be illustrative of the present invention and is not to be taken as limiting. Numerous other variations and modifications can be effected without departing from the true spirit and scope of the present invention.

What is claimed:

1. A strategically modified hepatitis B core protein conjugate comprising a strategically modified hepadnavirus nucleocapsid protein pendently linked to a hapten, wherein the strategically modified hepatitis B core protein comprises an amino acid sequence corresponding to the hepatitis B core protein amino acid sequence of SEQ ID NO:2 including the amino acid residues numbered about 10 to about 140 and additionally having an insert in the region corresponding to amino acid residues numbered about 50 to about 100, said insert (i) being 1 to about 40 amino acid residues in length, and (ii) containing a chemically-reactive amino acid residue, said hapten being pendently linked to said chemically-reactive amino acid residue.

2. The strategically modified hepatitis B core protein conjugate according to claim 1 wherein the insert is in the region corresponding to amino acid residues numbered about 70 to about 90.

3. The strategically modified hepatitis B core protein conjugate according to claim 1 wherein the insert is in the region corresponding to amino acid residues numbered 78 to 82.

4. The strategically modified hepatitis B core protein conjugate according to claim 1 wherein the hapten is a polypeptide hapten, chemical hapten or carbohydrate hapten.

5. The strategically modified hepatitis B core protein conjugate according to claim 1 wherein the hapten is a pathogen-related hapten.

6. The strategically modified hepatitis B core protein conjugate according to claim 5 wherein the strategically modified hepatitis B core protein further comprises a T cell stimulating amino acid residue sequence operatively linked to the carboxy terminus of said hepatitis B amino acid sequence.

7. The strategically modified hepatitis B core protein conjugate according to claim 6 wherein said T cell stimulating amino acid residue sequence is related to the same pathogen as the pendently linked pathogen-related hapten.

8. A strategically modified hepatitis B core protein particle comprising a strategically modified hepatitis B core protein subunit having an insert containing a chemically-reactive amino acid side chain, said insert not itself an antigenic determinant.

9. A strategically modified hepatitis B core protein particle conjugate comprising a plurality of strategically modified hepatitis B core protein subunits pendently linked to a hapten.

10. The strategically modified hepatitis B core protein particle conjugate according to claim 9 wherein about 0.1 to about 0.5 of the strategically modified hepatitis B core protein subunits are pendently linked to a hapten.

11. The strategically modified hepatitis B core protein particle conjugate according to claim 9 having a plurality of strategically modified hepatitis B core protein subunits that are pendently linked to different haptens.

12. The strategically modified hepatitis B core protein particle conjugate according to claim 9 wherein the strategically modified hepatitis B core protein subunit further comprises a T cell stimulating amino acid residue sequence peptide-bonded to the carboxy terminal residue of the amino acid sequence corresponding to said hepatitis B amino acid sequence.

13. The strategically modified hepatitis B core protein particle conjugate according to claim 12 wherein the T cell stimulating amino acid residue is from the same pathogen as the pendently linked hapten.

14. An immunogenic fusion protein conjugate comprising a polypeptide hapten pendently linked to a strategically modified hepatitis B core protein that comprises three peptide-linked domains, I, II and III from the N-terminus, wherein (a) Domain I corresponds to residues about 10 through 50 of the amino acid sequence of hepatitis B core protein of SEQ ID NO:2;

(b) Domain II is bonded to the carboxy terminal residue of Domain I and corresponds to residues 50 to 100 of said amino acid sequence of hepatitis B core protein that further contains a heterologous insert 1 to about 40 amino acid residues in length that includes a chemically-reactive amino acid residue; and (c) Domain III is bonded to the carboxy terminal residue of Domain II and corresponds to residues 100 to about 140 of the amino acid sequence of hepatitis B core protein.

15. An immunogenic fusion protein conjugate according to claim 14 wherein the strategically modified hepatitis B core protein further comprises a fourth peptide-linked domain, Domain IV, wherein (d) Domain IV is bonded to the carboxy terminal residue of Domain III and comprises a T cell epitope.

16. A strategically-modified hepatitis B core protein comprising an amino acid sequence corresponding to about amino acid residue 10 to about amino acid residue 140 of the hepatitis B amino acid sequence of SEQ ID NO:2 and having an amino acid sequence insert in the region corresponding to about residue 50 to about residue 100 of the hepatitis B, wherein the insert includes a chemically-reactive amino acid residue and the insert itself is not an antigenic determinant.

17. An inoculum comprising an immunogenic amount of a strategically modified hepatitis B core protein conjugate dissolved or dispersed in a pharmaceutically acceptable diluent, said strategically modified hepatitis B core protein conjugate comprising a hapten pendently linked to a strategically modified hepatitis B core protein, wherein the strategically modified hepatitis B core protein comprises an amino acid sequence corresponding to the hepatitis B core protein amino acid sequence of SEQ ID NO:2 including the amino acid residues numbered about 10 to about 140 and additionally having an insert in the region corresponding to amino acid residues numbered about 50 to about 100, said insert (i) being 1 to about 40 amino acid residues in length, and (ii) containing a chemically-reactive amino acid residue, said hapten being pendently linked to said chemically-reactive amino acid residue.

18. The inoculum according to claim 17 wherein said strategically modified hepatitis B core protein conjugate is present in the form of particles.

19. The inoculum according to claim 18 wherein said hapten is from a pathogen and wherein use of said inoculum in a mammalian host protects said mammalian host from said pathogen.

20. A process for inducing antibodies in an animal host comprising the steps of inoculating said animal host with an inoculum that comprises an immunogenic amount of a strategically modified hepatitis B core protein conjugate dissolved or dispersed in a pharmaceutically acceptable diluent, said strategically modified hepatitis B core protein conjugate comprising a hapten pendently linked to a strategically modified hepatitis B core protein, wherein the strategically modified hepatitis B core protein comprises an amino acid sequence corresponding to the hepatitis B core protein amino acid sequence of SEQ ID NO:2 including the amino acid residues numbered about 10 to about 140 and additionally having an insert in the region corresponding to amino acid residues numbered about 50 to about 100, said insert (i) being 1 to about 40 amino acid residues in length, and (ii) containing a chemically-reactive amino acid residue, said hapten being pendently linked to said strategically modified hepatitis B core protein through said chemically-reactive amino acid residue, and maintaining said animal for a time sufficient for antibodies to be induced.

21. The process according to claim 20 wherein said strategically modified hepatitis B core protein conjugate is present in the form of particles.

22. The process according to claim 21 wherein said hapten is from a pathogen and wherein the antibodies induced in said mammalian host protect said mammalian host from said pathogen.

* * * * *

SEQUENCE LISTING

<160> NUMBER OF SEQ ID NOS: 113

<210> SEQ ID NO 1
<211> LENGTH: 553
<212> TYPE: DNA
<213> ORGANISM: Hepatitis B virus
<220> FEATURE:
<221> NAME/KEY: CDS
<222> LOCATION: (1)..(549)
<300> PUBLICATION INFORMATION:
<303> JOURNAL: Nature
<304> VOLUME: 281
<306> PAGES: 646-
<307> DATE: 1979

<400> SEQUENCE: 1

```
atg gac atc gac cct tat aaa gaa ttt gga gct act gtg gag tta ctc        48
Met Asp Ile Asp Pro Tyr Lys Glu Phe Gly Ala Thr Val Glu Leu Leu
  1               5                  10                  15 tcg ttt ttg cct tct gac ttc ttt cct tca gta cga gat ctt cta gat        96
Ser Phe Leu Pro Ser Asp Phe Phe Pro Ser Val Arg Asp Leu Leu Asp
             20                  25                  30 acc gcc tca gct ctg tat cgg gaa gcc tta gag tct cct gag cat tgt       144
Thr Ala Ser Ala Leu Tyr Arg Glu Ala Leu Glu Ser Pro Glu His Cys
         35                  40                  45 tca cct cac cat act gca ctc agg caa gca att ctt tgc tgg ggg gaa       192
Ser Pro His His Thr Ala Leu Arg Gln Ala Ile Leu Cys Trp Gly Glu
     50                  55                  60 cta atg act cta gct acc tgg gtg ggt gtt aat ttg gaa gat cca gcg       240
Leu Met Thr Leu Ala Thr Trp Val Gly Val Asn Leu Glu Asp Pro Ala
 65                  70                  75                  80 tct aga gac cta gta gtc agt tat gtc aac act aat atg ggc cta aag       288
Ser Arg Asp Leu Val Val Ser Tyr Val Asn Thr Asn Met Gly Leu Lys
                 85                  90                  95 ttc agg caa ctc ttg tgg ttt cac att tct tgt ctc act ttt gga aga       336
```

```
Phe Arg Gln Leu Leu Trp Phe His Ile Ser Cys Leu Thr Phe Gly Arg
            100                 105                 110 gaa aca gtt ata gag tat ttg gtg tct ttc gga gtg tgg att cgc act      384
Glu Thr Val Ile Glu Tyr Leu Val Ser Phe Gly Val Trp Ile Arg Thr
            115                 120                 125 cct cca gct tat aga cca cca aat gcc cct atc cta tca aca ctt ccg      432
Pro Pro Ala Tyr Arg Pro Pro Asn Ala Pro Ile Leu Ser Thr Leu Pro
130                 135                 140 gag act act gtt gtt aga cga cga ggc agg tcc cct aga aga aga act      480
Glu Thr Thr Val Val Arg Arg Arg Gly Arg Ser Pro Arg Arg Arg Thr
145                 150                 155                 160 ccc tcg cct cgc aga cga agg tct caa tcg ccg cgt cgc aga aga tct      528
Pro Ser Pro Arg Arg Arg Ser Gln Ser Pro Arg Arg Arg Arg Ser
                165                 170                 175 caa tct cgg gaa tct caa tgt tagt                                     553
Gln Ser Arg Glu Ser Gln Cys
            180
```

<210> SEQ ID NO 2
<211> LENGTH: 183
<212> TYPE: PRT
<213> ORGANISM: Hepatitis B virus

<400> SEQUENCE: 2

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Arg Ser
                165                 170                 175

Gln Ser Arg Glu Ser Gln Cys
            180
```

<210> SEQ ID NO 3
<211> LENGTH: 552
<212> TYPE: DNA
<213> ORGANISM: Hepatitis B virus
<220> FEATURE:
<221> NAME/KEY: CDS
<222> LOCATION: (1)..(549)
<300> PUBLICATION INFORMATION:
<303> JOURNAL: Nucleic Acids Res.
<304> VOLUME: 11
<306> PAGES: 1747-

```
<307> DATE: 1983

<400> SEQUENCE: 3 atg gac att gac ccg tat aaa gaa ttt gga gca tct gtg gag tta ctc      48
Met Asp Ile Asp Pro Tyr Lys Glu Phe Gly Ala Ser Val Glu Leu Leu
  1               5                  10                  15 tct ttt ttg cct tct gac ttc ttt ccg tct att cga gat ctc ctt gac      96
Ser Phe Leu Pro Ser Asp Phe Phe Pro Ser Ile Arg Asp Leu Leu Asp
             20                  25                  30 acc gcc tct gct ctg tat cgg gag gcc tta gag tct ccg gaa cat tgt     144
Thr Ala Ser Ala Leu Tyr Arg Glu Ala Leu Glu Ser Pro Glu His Cys
         35                  40                  45 tca cct cac cat aca gca ctc agg caa gct att ctg tgt tgg ggt gag     192
Ser Pro His His Thr Ala Leu Arg Gln Ala Ile Leu Cys Trp Gly Glu
     50                  55                  60 tta atg aat ctg gcc acc tgg gtg gga agt aat ttg gaa gac cca gca     240
Leu Met Asn Leu Ala Thr Trp Val Gly Ser Asn Leu Glu Asp Pro Ala
 65                  70                  75                  80 tcc agg gaa tta gta gtc agc tat gtc aat gtt aat atg ggc cta aaa     288
Ser Arg Glu Leu Val Val Ser Tyr Val Asn Val Asn Met Gly Leu Lys
                 85                  90                  95 atc aga caa cta ttg tgg ttt cac att tcc tgc ctt act ttt gga aga     336
Ile Arg Gln Leu Leu Trp Phe His Ile Ser Cys Leu Thr Phe Gly Arg
            100                 105                 110 gaa act gtt ttg gag tat ttg gta tct ttt gga gtg tgg att cgc act     384
Glu Thr Val Leu Glu Tyr Leu Val Ser Phe Gly Val Trp Ile Arg Thr
        115                 120                 125 cct ccc gct tac aga cca cca aat gcc cct atc tta tca aca ctt ccg     432
Pro Pro Ala Tyr Arg Pro Pro Asn Ala Pro Ile Leu Ser Thr Leu Pro
    130                 135                 140 gaa act act gtt gtt aga cga cga ggc agg tcc cct aga aga aga act     480
Glu Thr Thr Val Val Arg Arg Arg Gly Arg Ser Pro Arg Arg Arg Thr
145                 150                 155                 160 ccc tcg cct cgc aga cga agg tct caa tcg ccg cgt cgc aga aga tct     528
Pro Ser Pro Arg Arg Arg Arg Ser Gln Ser Pro Arg Arg Arg Arg Ser
                165                 170                 175 caa tct cgg gaa tct caa tgt tag                                     552
Gln Ser Arg Glu Ser Gln Cys
            180

<210> SEQ ID NO 4
<211> LENGTH: 183
<212> TYPE: PRT
<213> ORGANISM: Hepatitis B virus

<400> SEQUENCE: 4

Met Asp Ile Asp Pro Tyr Lys Glu Phe Gly Ala Ser Val Glu Leu Leu
  1               5                  10                  15

Ser Phe Leu Pro Ser Asp Phe Phe Pro Ser Ile Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Asn Leu Ala Thr Trp Val Gly Ser Asn Leu Glu Asp Pro Ala
 65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
```

```
                  100                 105                 110
Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
            165                 170                 175

Gln Ser Arg Glu Ser Gln Cys
            180

<210> SEQ ID NO 5
<211> LENGTH: 558
<212> TYPE: DNA
<213> ORGANISM: Hepatitis B virus
<220> FEATURE:
<221> NAME/KEY: CDS
<222> LOCATION: (1)..(555)
<300> PUBLICATION INFORMATION:
<303> JOURNAL: Nucleic Acids Res.
<304> VOLUME: 11
<306> PAGES: 1747-
<307> DATE: 1983

<400> SEQUENCE: 5 atg gac att gac cct tat aaa gaa ttt gga gct act gtg gag tta ctc        48
Met Asp Ile Asp Pro Tyr Lys Glu Phe Gly Ala Thr Val Glu Leu Leu
 1               5                  10                  15 tcg ttt ttg cct tct gac ttc ttt cct tcc gta cga gat ctc cta gac        96
Ser Phe Leu Pro Ser Asp Phe Phe Pro Ser Val Arg Asp Leu Leu Asp
             20                  25                  30 acc gcc tca gct ctg tat cga gaa gcc tta gag tct cct gag cat tgc       144
Thr Ala Ser Ala Leu Tyr Arg Glu Ala Leu Glu Ser Pro Glu His Cys
         35                  40                  45 tca cct cac cat act gca ctc agg caa gcc att ctc tgc tgg ggg gaa       192
Ser Pro His His Thr Ala Leu Arg Gln Ala Ile Leu Cys Trp Gly Glu
     50                  55                  60 ttg atg act cta gct acc tgg gtg ggt aat aat ttg caa gat cca gca       240
Leu Met Thr Leu Ala Thr Trp Val Gly Asn Asn Leu Gln Asp Pro Ala
 65                  70                  75                  80 tcc aga gat cta gta gtc aat tat gtt aat act aac atg ggt tta aag       288
Ser Arg Asp Leu Val Val Asn Tyr Val Asn Thr Asn Met Gly Leu Lys
                 85                  90                  95 atc agg caa cta ttg tgg ttt cat ata tct tgc ctt act ttt gga aga       336
Ile Arg Gln Leu Leu Trp Phe His Ile Ser Cys Leu Thr Phe Gly Arg
            100                 105                 110 gag act gta ctt gaa tat ttg gtc tct ttc gga gtg tgg att cgc act       384
Glu Thr Val Leu Glu Tyr Leu Val Ser Phe Gly Val Trp Ile Arg Thr
        115                 120                 125 cct cca gcc tat aga cca cca aat gcc cct atc tta tca aca ctt ccg       432
Pro Pro Ala Tyr Arg Pro Pro Asn Ala Pro Ile Leu Ser Thr Leu Pro
    130                 135                 140 gaa act act gtt gtt aga cga cgg gac cga ggc agg tcc cct aga aga       480
Glu Thr Thr Val Val Arg Arg Arg Asp Arg Gly Arg Ser Pro Arg Arg
145                 150                 155                 160 aga act ccc tcg cct cgc aga cgc aga tct caa tcg ccg cgt cgc aga       528
Arg Thr Pro Ser Pro Arg Arg Arg Ser Gln Ser Pro Arg Arg Arg
                165                 170                 175 aga tct caa tct cgg gaa tct caa tgt tag                              558
Arg Ser Gln Ser Arg Glu Ser Gln Cys
```

```
                    180                 185

<210> SEQ ID NO 6
<211> LENGTH: 185
<212> TYPE: PRT
<213> ORGANISM: Hepatitis B virus

<400> SEQUENCE: 6

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
         50                  55                  60

Leu Met Thr Leu Ala Thr Trp Val Gly Asn Asn Leu Gln Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
                180                 185

<210> SEQ ID NO 7
<211> LENGTH: 188
<212> TYPE: PRT
<213> ORGANISM: Hepatitis B virus
<300> PUBLICATION INFORMATION:
<301> AUTHORS: Schodel, Florian
      et al.,
<302> TITLE: Animal Hepatitis B Viruses
<303> JOURNAL: Adv. Viral Oncol.
<304> VOLUME: 8
<306> PAGES: 73-102
<307> DATE: 1989

<400> SEQUENCE: 7

Met Asp Ile Asp Pro Tyr Lys Glu Phe Gly Ser Ser Tyr Gln Leu Leu
  1               5                  10                  15

Asn Phe Leu Pro Leu Asp Phe Phe Pro Asp Leu Asn Ala Leu Val Asp
                 20                  25                  30

Thr Ala Ala Ala Leu Tyr Glu Glu Glu Leu Thr Gly Arg Glu His Cys
             35                  40                  45

Ser Pro His His Thr Ala Ile Arg Gln Ala Leu Val Cys Trp Asp Glu
         50                  55                  60

Leu Thr Lys Leu Ile Ala Trp Met Ser Ser Asn Ile Thr Ser Glu Gln
 65                  70                  75                  80

Val Arg Thr Ile Ile Val Asn His Val Asn Asp Thr Trp Gly Leu Lys
                 85                  90                  95
```

```
Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
                180                 185

<210> SEQ ID NO 8
<211> LENGTH: 654
<212> TYPE: DNA
<213> ORGANISM: Hepatitis B virus
<220> FEATURE:
<221> NAME/KEY: CDS
<222> LOCATION: (1)..(651)
<300> PUBLICATION INFORMATION:
<302> TITLE: Animal Hepatitis B Viruses
<303> JOURNAL: Adv. Viral Oncol.
<304> VOLUME: 8
<306> PAGES: 73-102
<307> DATE: 1989

<400> SEQUENCE: 8 atg tat ctt ttt cac ctg tgc ctt gtt ttt gcc tgt gtt cca tgt cct      48
Met Tyr Leu Phe His Leu Cys Leu Val Phe Ala Cys Val Pro Cys Pro
  1               5                  10                  15 act gtt caa gcc tcc aag ctg tgc ctt gga tgg ctt tgg gac atg gac      96
Thr Val Gln Ala Ser Lys Leu Cys Leu Gly Trp Leu Trp Asp Met Asp
             20                  25                  30 ata gat ccc tat aaa gaa ttt ggt tct tct tat cag ttg ttg aat ttt     144
Ile Asp Pro Tyr Lys Glu Phe Gly Ser Ser Tyr Gln Leu Leu Asn Phe
         35                  40                  45 ctt cct ttg gac ttt ttt cct gat ctc aat gca ttg gtg gac act gct     192
Leu Pro Leu Asp Phe Phe Pro Asp Leu Asn Ala Leu Val Asp Thr Ala
     50                  55                  60 gct gct ctt tat gaa gaa gaa tta aca ggt agg gag cat tgt tct cct     240
Ala Ala Leu Tyr Glu Glu Glu Leu Thr Gly Arg Glu His Cys Ser Pro
 65                  70                  75                  80 cat cat act gct att aga cag gcc tta gtg tgt tgg gaa gaa tta act     288
His His Thr Ala Ile Arg Gln Ala Leu Val Cys Trp Glu Glu Leu Thr
                 85                  90                  95 aga tta att aca tgg atg agt gaa aat aca aca gaa gaa gtt aga aga     336
Arg Leu Ile Thr Trp Met Ser Glu Asn Thr Thr Glu Glu Val Arg Arg
            100                 105                 110 att att gtt gat cat gtc aat aat act tgg gga ctt aaa gta aga cag     384
Ile Ile Val Asp His Val Asn Asn Thr Trp Gly Leu Lys Val Arg Gln
        115                 120                 125 act tta tgg ttt cat tta tca tgt ctt act ttt gga caa cac aca gtt     432
Thr Leu Trp Phe His Leu Ser Cys Leu Thr Phe Gly Gln His Thr Val
    130                 135                 140 caa gaa ttt ttg gtt agt ttt gga gta tgg att aga act cca gct cct     480
Gln Glu Phe Leu Val Ser Phe Gly Val Trp Ile Arg Thr Pro Ala Pro
145                 150                 155                 160 tat aga cca cct aat gca ccc att tta tca act ctt ccg gaa cat aca     528
Tyr Arg Pro Pro Asn Ala Pro Ile Leu Ser Thr Leu Pro Glu His Thr
                165                 170                 175
```

```
gtc att agg aga aga gga ggt tca aga gct gct agg tcc ccc cga aga    576
Val Ile Arg Arg Arg Gly Gly Ser Arg Ala Ala Arg Ser Pro Arg Arg
            180                 185                 190 cgc act ccc tct cct cgc agg aga agg tct caa tca ccg cgt cgc aga    624
Arg Thr Pro Ser Pro Arg Arg Arg Ser Gln Ser Pro Arg Arg Arg
        195                 200                 205 cgc tct caa tct cca gct tcc aac tgc tga                            654
Arg Ser Gln Ser Pro Ala Ser Asn Cys
    210                 215

<210> SEQ ID NO 9
<211> LENGTH: 217
<212> TYPE: PRT
<213> ORGANISM: Hepatitis B virus

<400> SEQUENCE: 9

Met Tyr Leu Phe His Leu Cys Leu Val Phe Ala Cys Val Pro Cys Pro
 1               5                  10                  15

Thr Val Gln Ala Ser Lys Leu Cys Leu Gly Trp Leu Trp Asp Met Asp
             20                  25                  30

Ile Asp Pro Tyr Lys Glu Phe Gly Ser Ser Tyr Gln Leu Leu Asn Phe
         35                  40                  45

Leu Pro Leu Asp Phe Phe Pro Asp Leu Asn Ala Leu Val Asp Thr Ala
 50                  55                  60

Ala Ala Leu Tyr Glu Glu Glu Leu Thr Gly Arg Glu His Cys Ser Pro
65                  70                  75                  80

His His Thr Ala Ile Arg Gln Ala Leu Val Cys Trp Glu Glu Leu Thr
                 85                  90                  95

Arg Leu Ile Thr Trp Met Ser Glu Asn Thr Thr Glu Glu Val Arg Arg
            100                 105                 110

Ile Ile Val Asp His Val Asn Asn Thr Trp Gly Leu Lys Val Arg Gln
        115                 120                 125

Thr Leu Trp Phe His Leu Ser Cys Leu Thr Phe Gly Gln His Thr Val
    130                 135                 140

Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                165                 170                 175

Val Ile Arg Arg Arg Gly Gly Ser Arg Ala Ala Arg Ser Pro Arg Arg
            180                 185                 190

Arg Thr Pro Ser Pro Arg Arg Arg Ser Gln Ser Pro Arg Arg Arg
        195                 200                 205

Arg Ser Gln Ser Pro Ala Ser Asn Cys
    210                 215

<210> SEQ ID NO 10
<211> LENGTH: 918
<212> TYPE: DNA
<213> ORGANISM: Hepatitis B virus
<220> FEATURE:
<221> NAME/KEY: CDS
<222> LOCATION: (1)..(915)

<400> SEQUENCE: 10 atg tgg tct cta aga tta cac ccc tct cca ttc gga gct gcg tgc caa     48
Met Trp Ser Leu Arg Leu His Pro Ser Pro Phe Gly Ala Ala Cys Gln
 1               5                  10                  15 ggt atc ttt acg tcg acc tcg ctg ttg ttc ctt gtg act gta cct ttg     96
```

```
                                          -continued

Gly Ile Phe Thr Ser Thr Ser Leu Leu Phe Leu Val Thr Val Pro Leu
         20                  25                  30 gta tgt acc att gtt tat gat tct tgc tta tat atg gat gtc aat gct       144
Val Cys Thr Ile Val Tyr Asp Ser Cys Leu Tyr Met Asp Val Asn Ala
         35                  40                  45 tca aga gct tta gca aat gta tat gat ctg cca gat gat ttc ttt cct       192
Ser Arg Ala Leu Ala Asn Val Tyr Asp Leu Pro Asp Asp Phe Phe Pro
 50                  55                  60 cag att gat gat ctt gtt aga gat gct aag gat gct tta gaa cct tat       240
Gln Ile Asp Asp Leu Val Arg Asp Ala Lys Asp Ala Leu Glu Pro Tyr
 65                  70                  75                  80 tgg aaa gcc gaa aca ata aag aaa cat gtt tta att gct act cac ttt       288
Trp Lys Ala Glu Thr Ile Lys Lys His Val Leu Ile Ala Thr His Phe
                 85                  90                  95 gtg gat ttg att gag gac ttc tgg cag acc act cag ggt atg agc caa       336
Val Asp Leu Ile Glu Asp Phe Trp Gln Thr Thr Gln Gly Met Ser Gln
                100                 105                 110 att gca gac gcc ctc cga gca gta att cca cct act acc gta cca gta       384
Ile Ala Asp Ala Leu Arg Ala Val Ile Pro Pro Thr Thr Val Pro Val
                115                 120                 125 ccg gag ggt ttt ctc att act cat agt gag gca gaa gag atc ccc ttg       432
Pro Glu Gly Phe Leu Ile Thr His Ser Glu Ala Glu Glu Ile Pro Leu
130                 135                 140 aac gat ctc ttt tca aat caa gag gag agg ata gtc aat ttc caa cct       480
Asn Asp Leu Phe Ser Asn Gln Glu Glu Arg Ile Val Asn Phe Gln Pro
145                 150                 155                 160 gac tat ccc att aca gct aga att cat acc cac tta cgt gtt tat act       528
Asp Tyr Pro Ile Thr Ala Arg Ile His Thr His Leu Arg Val Tyr Thr
                165                 170                 175 aaa ttg aat gaa caa gct ttg gac aaa gct cgc aga ttg ctt tgg tgg       576
Lys Leu Asn Glu Gln Ala Leu Asp Lys Ala Arg Arg Leu Leu Trp Trp
                180                 185                 190 cat tac aat tgc ctc ctc tgg gga gaa gcc act gtt aca aat tat att       624
His Tyr Asn Cys Leu Leu Trp Gly Glu Ala Thr Val Thr Asn Tyr Ile
                195                 200                 205 tct cgc ctc cgt act tgg ctt tct act ccc gaa aaa tat cga ggc aag       672
Ser Arg Leu Arg Thr Trp Leu Ser Thr Pro Glu Lys Tyr Arg Gly Lys
210                 215                 220 gat gcc cca acc att gaa gca atc act aga cca atc cag gtg gct caa       720
Asp Ala Pro Thr Ile Glu Ala Ile Thr Arg Pro Ile Gln Val Ala Gln
225                 230                 235                 240 gga ggc aga aat caa act aag gga act aga aaa cct cgt gga ctc gaa       768
Gly Gly Arg Asn Gln Thr Lys Gly Thr Arg Lys Pro Arg Gly Leu Glu
                245                 250                 255 cct aga aga cga aag gtt aaa acc aca gtt gtc tat ggg aga aga cgt       816
Pro Arg Arg Arg Lys Val Lys Thr Thr Val Val Tyr Gly Arg Arg Arg
                260                 265                 270 tct aag tcc cga ggc agg aga tcc tct cca tcc caa cgt gcg ggc tcc       864
Ser Lys Ser Arg Gly Arg Arg Ser Ser Pro Ser Gln Arg Ala Gly Ser
                275                 280                 285 cct ctc cca cgt aat cgg gga aac cag aca cga tcc ccc tca cct agg       912
Pro Leu Pro Arg Asn Arg Gly Asn Gln Thr Arg Ser Pro Ser Pro Arg
        290                 295                 300 gaa tag                                                                918
Glu
305

<210> SEQ ID NO 11
<211> LENGTH: 305
<212> TYPE: PRT
```

<213> ORGANISM: Hepatitis B virus

<400> SEQUENCE: 11

```
Met Trp Ser Leu Arg Leu His Pro Ser Pro Phe Gly Ala Ala Cys Gln
 1               5                   10                  15

Gly Ile Phe Thr Ser Thr Ser Leu Leu Phe Leu Val Thr Val Pro Leu
                20                  25                  30

Val Cys Thr Ile Val Tyr Asp Ser Cys Leu Tyr Met Asp Val Asn Ala
                35                  40                  45

Ser Arg Ala Leu Ala Asn Val Tyr Asp Leu Pro Asp Asp Phe Phe Pro
        50                  55                  60

Gln Ile Asp Asp Leu Val Arg Asp Ala Lys Asp Ala Leu Glu Pro Tyr
65                  70                  75                  80

Trp Lys Ala Glu Thr Ile Lys Lys His Val Leu Ile Ala Thr His Phe
                85                  90                  95

Val Asp Leu Ile Glu Asp Phe Trp Gln Thr Thr Gln Gly Met Ser Gln
                100                 105                 110

Ile Ala Asp Ala Leu Arg Ala Val Ile Pro Pro Thr Thr Val Pro Val
            115                 120                 125

Pro Glu Gly Phe Leu Ile Thr His Ser Glu Ala Glu Ile Pro Leu
        130                 135                 140

Asn Asp Leu Phe Ser Asn Gln Glu Glu Arg Ile Val Asn Phe Gln Pro
145                 150                 155                 160

Asp Tyr Pro Ile Thr Ala Arg Ile His Thr His Leu Arg Val Tyr Thr
                165                 170                 175

Lys Leu Asn Glu Gln Ala Leu Asp Lys Ala Arg Arg Leu Leu Trp Trp
                180                 185                 190

His Tyr Asn Cys Leu Leu Trp Gly Glu Ala Thr Val Thr Asn Tyr Ile
            195                 200                 205

Ser Arg Leu Arg Thr Trp Leu Ser Thr Pro Glu Lys Tyr Arg Gly Lys
        210                 215                 220

Asp Ala Pro Thr Ile Glu Ala Ile Thr Arg Pro Ile Gln Val Ala Gln
225                 230                 235                 240

Gly Gly Arg Asn Gln Thr Lys Gly Thr Arg Lys Pro Arg Gly Leu Glu
                245                 250                 255

Pro Arg Arg Arg Lys Val Lys Thr Thr Val Val Tyr Gly Arg Arg Arg
                260                 265                 270

Ser Lys Ser Arg Gly Arg Arg Ser Ser Pro Ser Gln Arg Ala Gly Ser
            275                 280                 285

Pro Leu Pro Arg Asn Arg Gly Asn Gln Thr Arg Ser Pro Ser Pro Arg
        290                 295                 300

Glu
305
```

<210> SEQ ID NO 12
<211> LENGTH: 918
<212> TYPE: DNA
<213> ORGANISM: Hepatitis B virus
<220> FEATURE:
<221> NAME/KEY: CDS
<222> LOCATION: (1)..(915)

<400> SEQUENCE: 12

```
atg tgg aac tta aga att aca ccc ctc tcc ttc gga gct gct tgc caa    48
Met Trp Asn Leu Arg Ile Thr Pro Leu Ser Phe Gly Ala Ala Cys Gln
 1               5                   10                  15
```

```
ggt atc ttt acg tct aca ttg ctg ttg tcg tgt gtg act gta cct ttg        96
Gly Ile Phe Thr Ser Thr Leu Leu Leu Ser Cys Val Thr Val Pro Leu
         20                  25                  30 gta tgt acc att gtt tat gat tct tgc tta tat atg gat atc aat gct       144
Val Cys Thr Ile Val Tyr Asp Ser Cys Leu Tyr Met Asp Ile Asn Ala
     35                  40                  45 tct aga gcc tta gcc aat gtg tat gat cta cca gat gat ttc ttt cca       192
Ser Arg Ala Leu Ala Asn Val Tyr Asp Leu Pro Asp Asp Phe Phe Pro
 50                  55                  60 aaa ata gat gat ctt gtt aga gat gct aaa gac gct tta gag cct tat       240
Lys Ile Asp Asp Leu Val Arg Asp Ala Lys Asp Ala Leu Glu Pro Tyr
 65                  70                  75                  80 tgg aaa tca gat tca ata aag aaa cat gtt ttg att gca act cac ttt       288
Trp Lys Ser Asp Ser Ile Lys Lys His Val Leu Ile Ala Thr His Phe
             85                  90                  95 gtg gat ctc att gaa gac ttc tgg cag act aca cag ggc atg cat gaa       336
Val Asp Leu Ile Glu Asp Phe Trp Gln Thr Thr Gln Gly Met His Glu
            100                 105                 110 ata gcc gaa tca tta aga gct gtt ata cct ccc act act act cct gtt       384
Ile Ala Glu Ser Leu Arg Ala Val Ile Pro Pro Thr Thr Thr Pro Val
        115                 120                 125 cca ccg ggt tat ctt att cag cac gag gaa gct gaa gag ata cct ttg       432
Pro Pro Gly Tyr Leu Ile Gln His Glu Glu Ala Glu Glu Ile Pro Leu
    130                 135                 140 gga gat tta ttt aaa cac caa gaa gaa agg ata gta agt ttc caa ccc       480
Gly Asp Leu Phe Lys His Gln Glu Glu Arg Ile Val Ser Phe Gln Pro
145                 150                 155                 160 gac tat ccg att acg gct aga att cat gct cat ttg aaa gct tat gca       528
Asp Tyr Pro Ile Thr Ala Arg Ile His Ala His Leu Lys Ala Tyr Ala
                165                 170                 175 aaa att aac gag gaa tca ctg gat agg gct agg aga ttg ctt tgg tgg       576
Lys Ile Asn Glu Glu Ser Leu Asp Arg Ala Arg Arg Leu Leu Trp Trp
            180                 185                 190 cat tac aac tgt tta ctg tgg gga gaa gct caa gtt act aac tat att       624
His Tyr Asn Cys Leu Leu Trp Gly Glu Ala Gln Val Thr Asn Tyr Ile
        195                 200                 205 tct cgt ttg cgt act tgg ttg tca act cct gag aaa tat aga ggt aga       672
Ser Arg Leu Arg Thr Trp Leu Ser Thr Pro Glu Lys Tyr Arg Gly Arg
    210                 215                 220 gat gcc ccg acc att gaa gca atc act aga cca atc cag gtg gct cag       720
Asp Ala Pro Thr Ile Glu Ala Ile Thr Arg Pro Ile Gln Val Ala Gln
225                 230                 235                 240 gga ggc aga aaa aca act acg ggt act aga aaa cct cgt gga ctc gaa       768
Gly Gly Arg Lys Thr Thr Thr Gly Thr Arg Lys Pro Arg Gly Leu Glu
                245                 250                 255 cct aga aga aga aaa gtt aaa acc aca gtt gtc tat ggg aga aga cgt       816
Pro Arg Arg Arg Lys Val Lys Thr Thr Val Val Tyr Gly Arg Arg Arg
            260                 265                 270 tca aag tcc cgg gaa agg aga gcc cct aca ccc caa cgt gcg ggc tcc       864
Ser Lys Ser Arg Glu Arg Arg Ala Pro Thr Pro Gln Arg Ala Gly Ser
        275                 280                 285 cct ctc cca cgt agt tcg agc agc cac cat aga tct ccc tcg cct agg       912
Pro Leu Pro Arg Ser Ser Ser Ser His His Arg Ser Pro Ser Pro Arg
    290                 295                 300 aaa taa                                                               918
Lys
305

<210> SEQ ID NO 13
<211> LENGTH: 305
```

```
<212> TYPE: PRT
<213> ORGANISM: Hepatitis B virus

<400> SEQUENCE: 13

Met Trp Asn Leu Arg Ile Thr Pro Leu Ser Phe Gly Ala Ala Cys Gln
 1               5                  10                  15

Gly Ile Phe Thr Ser Thr Leu Leu Ser Cys Val Thr Val Pro Leu
                20                  25                  30

Val Cys Thr Ile Val Tyr Asp Ser Cys Leu Tyr Met Asp Ile Asn Ala
                35                  40                  45

Ser Arg Ala Leu Ala Asn Val Tyr Asp Leu Pro Asp Phe Phe Pro
        50                  55                  60

Lys Ile Asp Asp Leu Val Arg Asp Ala Lys Asp Ala Leu Glu Pro Tyr
 65                  70                  75                  80

Trp Lys Ser Asp Ser Ile Lys Lys His Val Leu Ile Ala Thr His Phe
                85                  90                  95

Val Asp Leu Ile Glu Asp Phe Trp Gln Thr Thr Gln Gly Met His Glu
                100                 105                 110

Ile Ala Glu Ser Leu Arg Ala Val Ile Pro Pro Thr Thr Thr Pro Val
                115                 120                 125

Pro Pro Gly Tyr Leu Ile Gln His Glu Glu Ala Glu Glu Ile Pro Leu
    130                 135                 140

Gly Asp Leu Phe Lys His Gln Glu Glu Arg Ile Val Ser Phe Gln Pro
145                 150                 155                 160

Asp Tyr Pro Ile Thr Ala Arg Ile His Ala His Leu Lys Ala Tyr Ala
                165                 170                 175

Lys Ile Asn Glu Glu Ser Leu Asp Arg Ala Arg Arg Leu Leu Trp Trp
                180                 185                 190

His Tyr Asn Cys Leu Leu Trp Gly Glu Ala Gln Val Thr Asn Tyr Ile
                195                 200                 205

Ser Arg Leu Arg Thr Trp Leu Ser Thr Pro Glu Lys Tyr Arg Gly Arg
    210                 215                 220

Asp Ala Pro Thr Ile Glu Ala Ile Thr Arg Pro Ile Gln Val Ala Gln
225                 230                 235                 240

Gly Gly Arg Lys Thr Thr Thr Gly Thr Arg Lys Pro Arg Gly Leu Glu
                245                 250                 255

Pro Arg Arg Arg Lys Val Lys Thr Thr Val Val Tyr Gly Arg Arg Arg
                260                 265                 270

Ser Lys Ser Arg Glu Arg Arg Ala Pro Thr Pro Gln Arg Ala Gly Ser
    275                 280                 285

Pro Leu Pro Arg Ser Ser Ser His His Arg Ser Pro Ser Pro Arg
    290                 295                 300

Lys
305

<210> SEQ ID NO 14
<211> LENGTH: 37
<212> TYPE: PRT
<213> ORGANISM: Influenza virus

<400> SEQUENCE: 14

Ser Ile Met Arg Ser Asp Ala Pro Ile Gly Thr Cys Ser Ser Glu Cys
 1               5                  10                  15

Ile Thr Pro Asn Gly Ser Ile Pro Asn Asp Lys Pro Phe Gln Asn Val
                20                  25                  30
```

-continued

```
Asn Lys Ile Thr Tyr
            35

<210> SEQ ID NO 15
<211> LENGTH: 29
<212> TYPE: PRT
<213> ORGANISM: Influenza virus

<400> SEQUENCE: 15

Arg Gly Ile Phe Gly Ala Ile Ala Gly Phe Ile Glu Asn Gly Trp Glu
  1               5                  10                  15

Gly Met Ile Asp Gly Trp Tyr Gly Phe Arg His Gln Asn
            20                  25

<210> SEQ ID NO 16
<211> LENGTH: 10
<212> TYPE: PRT
<213> ORGANISM: Influenza virus

<400> SEQUENCE: 16

Glu Lys Gln Thr Arg Gly Ile Phe Gly Ala
  1               5                  10

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Hepatitis B
      virus PCR primer with an  NcoI restriction site

<400> SEQUENCE: 17
ttgggccatg gacatcgacc tta                                              23

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Hepatitis B
      virus PCR primer with an EcoRI  restriction site

<400> SEQUENCE: 18
gcggaattcc atcttccaaa ttaacaccca c                                     31

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Hepatitis B
      virus PCR primer with EcoRI and SacI restriction sites and an
      inserted lysine codon

<400> SEQUENCE: 19
cgcgaattca aaagagctc ccagcgtcta gagagaccta g                           41

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Hepatitis B
      virus PCR primer with HindIII restriction site

<400> SEQUENCE: 20
```

```
cgcaagctta aacaacagta gtctccggaa g                    31
```

```
<210> SEQ ID NO 21
<211> LENGTH: 14
<212> TYPE: PRT
<213> ORGANISM: Hepatitis B virus

<400> SEQUENCE: 21

Cys Gln Glu Lys Gln Leu Asp Glu Asn Ala Asn Val Gln Leu
 1               5                  10

<210> SEQ ID NO 22
<211> LENGTH: 13
<212> TYPE: PRT
<213> ORGANISM: Hepatitis B virus

<400> SEQUENCE: 22

Cys Ser Lys Lys Gly Pro Arg Ala Ser Gly Asn Leu Ile
 1               5                  10

<210> SEQ ID NO 23
<211> LENGTH: 19
<212> TYPE: PRT
<213> ORGANISM: Hepatitis B virus

<400> SEQUENCE: 23

Cys Leu Thr Glu His Arg Met Thr Trp Asp Pro Ala Gln Pro Pro Arg
 1               5                  10                  15

Asp Leu Thr

<210> SEQ ID NO 24
<211> LENGTH: 22
<212> TYPE: PRT
<213> ORGANISM: Hepatitis B virus

<400> SEQUENCE: 24

Cys Val Lys Arg Met Lys Glu Ser Arg Leu Glu Asp Thr Gln Lys His
 1               5                  10                  15

Arg Val Asp Phe Leu Gln
            20

<210> SEQ ID NO 25
<211> LENGTH: 15
<212> TYPE: PRT
<213> ORGANISM: Streptococcus pneumoniae
<300> PUBLICATION INFORMATION:
<310> PATENT DOCUMENT NUMBER: EP-0 786 521-A

<400> SEQUENCE: 25

Lys Leu Glu Glu Leu Ser Asp Lys Ile Asp Glu Leu Asp Ala Glu
 1               5                  10                  15

<210> SEQ ID NO 26
<211> LENGTH: 35
<212> TYPE: PRT
<213> ORGANISM: Streptococcus pneumoniae
<300> PUBLICATION INFORMATION:
<310> PATENT DOCUMENT NUMBER: EP-0 786 521-A

<400> SEQUENCE: 26

Gln Lys Lys Tyr Asp Glu Asp Gln Lys Lys Thr Glu Glu Lys Ala Ala
 1               5                  10                  15

Leu Glu Lys Ala Ala Ser Glu Glu Met Asp Lys Ala Val Ala Ala Val
            20                  25                  30
```

Gln Gln Ala
        35

<210> SEQ ID NO 27
<211> LENGTH: 31
<212> TYPE: PRT
<213> ORGANISM: Cryptosporidium parvum
<300> PUBLICATION INFORMATION:
<310> PATENT DOCUMENT NUMBER: WO 98/07320

<400> SEQUENCE: 27

Gln Asp Lys Pro Ala Asp Ala Pro Ala Ala Glu Ala Pro Ala Ala Glu
 1               5                  10                  15

Pro Ala Ala Glu Pro Ala Ala Gln Gln Asp Lys Pro Ala Asp Ala
            20                  25                  30

<210> SEQ ID NO 28
<211> LENGTH: 16
<212> TYPE: PRT
<213> ORGANISM: Human immunodeficiency virus
<300> PUBLICATION INFORMATION:
<310> PATENT DOCUMENT NUMBER: US 5,639,854

<400> SEQUENCE: 28

Gly Pro Lys Glu Pro Phe Arg Asp Tyr Val Asp Arg Phe Tyr Lys Cys
 1               5                  10                  15

<210> SEQ ID NO 29
<211> LENGTH: 17
<212> TYPE: PRT
<213> ORGANISM: Human immunodeficiency virus
<300> PUBLICATION INFORMATION:
<310> PATENT DOCUMENT NUMBER: WO 98/07320

<400> SEQUENCE: 29

Arg Lys Arg Ile His Ile Gly Pro Gly Arg Ala Phe Tyr Ile Thr Lys
 1               5                  10                  15

Asn

<210> SEQ ID NO 30
<211> LENGTH: 31
<212> TYPE: PRT
<213> ORGANISM: Foot-and-mouth disease virus
<300> PUBLICATION INFORMATION:
<310> PATENT DOCUMENT NUMBER: US 4,544,500

<400> SEQUENCE: 30

Tyr Asn Gly Glu Cys Arg Tyr Asn Arg Asn Ala Val Pro Asn Leu Arg
 1               5                  10                  15

Gly Asp Leu Gln Val Leu Ala Gln Lys Val Ala Arg Thr Leu Pro
            20                  25                  30

<210> SEQ ID NO 31
<211> LENGTH: 17
<212> TYPE: PRT
<213> ORGANISM: Corynebacterium diphtheriae
<300> PUBLICATION INFORMATION:
<310> PATENT DOCUMENT NUMBER: EP-0 399 011-B1

<400> SEQUENCE: 31

Phe Gln Val Val His Asn Ser Tyr Asn Arg Pro Ala Tyr Ser Pro Gly
 1               5                  10                  15

Cys

```
<210> SEQ ID NO 32
<211> LENGTH: 25
<212> TYPE: PRT
<213> ORGANISM: Borrelia burgdorferi
<300> PUBLICATION INFORMATION:
<301> AUTHORS: Bockenstedt, L. K.
      et al.,
<303> JOURNAL: J. Immunol.
<304> VOLUME: 157
<305> ISSUE: 12
<306> PAGES: 5496-
<307> DATE: (1966)

<400> SEQUENCE: 32

Val Glu Ile Lys Glu Gly Thr Val Thr Leu Lys Arg Glu Ile Asp Lys
 1               5                  10                  15

Asn Gly Lys Val Thr Val Ser Leu Cys
            20                  25

<210> SEQ ID NO 33
<211> LENGTH: 19
<212> TYPE: PRT
<213> ORGANISM: Borrelia burgdorferi
<300> PUBLICATION INFORMATION:
<301> AUTHORS: Zhong, W.
      et al.,
<303> JOURNAL: Eur. J. Immunol.
<304> VOLUME: 26
<305> ISSUE: 11
<306> PAGES: 2749-
<307> DATE: 1996

<400> SEQUENCE: 33

Thr Leu Ser Lys Asn Ile Ser Lys Ser Gly Glu Val Ser Val Glu Leu
 1               5                  10                  15

Asn Asp Cys

<210> SEQ ID NO 34
<211> LENGTH: 11
<212> TYPE: PRT
<213> ORGANISM: Influenza A virus
<300> PUBLICATION INFORMATION:
<301> AUTHORS: Brumeanu, T. D.
<303> JOURNAL: Immunotechnology
<304> VOLUME: 2
<305> ISSUE: 2
<306> PAGES: 85-
<307> DATE: (1996)

<400> SEQUENCE: 34

Ser Ser Val Ser Ser Phe Glu Arg Phe Glu Cys
 1               5                  10

<210> SEQ ID NO 35
<211> LENGTH: 10
<212> TYPE: PRT
<213> ORGANISM: Influenza A virus
<300> PUBLICATION INFORMATION:
<301> AUTHORS: Brumeanu, T. D.
<303> JOURNAL: Immunotechnology
<304> VOLUME: 2
<305> ISSUE: 2
<306> PAGES: 85-
<307> DATE: (1996)

<400> SEQUENCE: 35

Tyr Arg Asn Leu Leu Trp Leu Thr Glu Lys
 1               5                  10
```

-continued

```
<210> SEQ ID NO 36
<211> LENGTH: 142
<212> TYPE: PRT
<213> ORGANISM: Yersinia pestis
<300> PUBLICATION INFORMATION:
<301> AUTHORS: Hill, J.
      et al.,
<303> JOURNAL: Infect. Immun.
<304> VOLUME: 65
<305> ISSUE: 11
<306> PAGES: 4476-
<307> DATE: (1997)

<400> SEQUENCE: 36

Asp Ile Leu Lys Val Ile Val Asp Ser Met Asn His His Gly Asp Ala
  1               5                  10                  15

Arg Ser Lys Leu Arg Glu Glu Leu Ala Glu Leu Thr Ala Glu Leu Lys
             20                  25                  30

Ile Tyr Ser Val Ile Gln Ala Glu Ile Asn Lys His Leu Ser Ser Ser
         35                  40                  45

Gly Thr Ile Asn Ile His Asp Lys Ser Ile Asn Leu Met Asp Lys Asn
     50                  55                  60

Leu Tyr Gly Tyr Thr Asp Glu Glu Ile Phe Lys Ala Ser Ala Glu Tyr
 65                  70                  75                  80

Lys Ile Leu Glu Lys Met Pro Gln Thr Thr Ile Gln Val Asp Gly Ser
                 85                  90                  95

Glu Lys Lys Ile Val Ser Ile Lys Asp Phe Leu Gly Ser Glu Asn Lys
            100                 105                 110

Arg Thr Gly Ala Leu Gly Asn Leu Lys Asn Ser Tyr Ser Tyr Asn Lys
        115                 120                 125

Asp Asn Asn Glu Leu Ser His Phe Ala Thr Thr Cys Ser Asp
    130                 135                 140

<210> SEQ ID NO 37
<211> LENGTH: 19
<212> TYPE: PRT
<213> ORGANISM: Haemophilus influenzae
<300> PUBLICATION INFORMATION:
<310> PATENT DOCUMENT NUMBER: EP-0 432 220-B1

<400> SEQUENCE: 37

Cys Ser Ser Ser Asn Asn Asp Ala Ala Gly Asn Gly Ala Ala Gln Phe
  1               5                  10                  15

Gly Gly Tyr

<210> SEQ ID NO 38
<211> LENGTH: 11
<212> TYPE: PRT
<213> ORGANISM: Haemophilus influenzae
<300> PUBLICATION INFORMATION:
<310> PATENT DOCUMENT NUMBER: EP-0 432 220-B1

<400> SEQUENCE: 38

Asn Lys Leu Gly Thr Val Ser Tyr Gly Glu Glu
  1               5                  10

<210> SEQ ID NO 39
<211> LENGTH: 16
<212> TYPE: PRT
<213> ORGANISM: Haemophilus influenzae
<300> PUBLICATION INFORMATION:
<310> PATENT DOCUMENT NUMBER: EP-0 432 220-B1
```

-continued

<400> SEQUENCE: 39

Asn Asp Glu Ala Ala Tyr Ser Lys Asn Arg Arg Ala Val Leu Ala Tyr
 1               5                  10                  15

<210> SEQ ID NO 40
<211> LENGTH: 28
<212> TYPE: PRT
<213> ORGANISM: Moraxella catarrhalis
<300> PUBLICATION INFORMATION:
<310> PATENT DOCUMENT NUMBER: WO 98/06851

<400> SEQUENCE: 40

Leu Asp Ile Glu Lys Asp Lys Lys Arg Thr Asp Glu Gln Leu Gln
 1               5                  10                  15

Ala Glu Leu Asp Asp Lys Tyr Ala Gly Lys Gly Tyr
            20                  25

<210> SEQ ID NO 41
<211> LENGTH: 28
<212> TYPE: PRT
<213> ORGANISM: Moraxella catarrhalis
<300> PUBLICATION INFORMATION:
<310> PATENT DOCUMENT NUMBER: WO 98/06851

<400> SEQUENCE: 41

Leu Asp Ile Glu Lys Asn Lys Lys Arg Thr Glu Ala Glu Leu Gln
 1               5                  10                  15

Ala Glu Leu Asp Asp Lys Tyr Ala Gly Lys Gly Tyr
            20                  25

<210> SEQ ID NO 42
<211> LENGTH: 28
<212> TYPE: PRT
<213> ORGANISM: Moraxella catarrhalis
<300> PUBLICATION INFORMATION:
<310> PATENT DOCUMENT NUMBER: WO 98/06851

<400> SEQUENCE: 42

Ile Asp Ile Glu Lys Lys Gly Lys Ile Arg Thr Glu Ala Glu Leu Leu
 1               5                  10                  15

Ala Glu Leu Asn Lys Asp Tyr Pro Gly Gln Gly Tyr
            20                  25

<210> SEQ ID NO 43
<211> LENGTH: 25
<212> TYPE: PRT
<213> ORGANISM: Porphyromonas gingivalis
<300> PUBLICATION INFORMATION:
<304> VOLUME: 110
<305> ISSUE: 2
<306> PAGES: 285-
<307> DATE: 1997

<400> SEQUENCE: 43

Gly Val Ser Pro Lys Val Cys Lys Asp Val Thr Val Glu Gly Ser Asn
 1               5                  10                  15

Glu Phe Ala Pro Val Gln Asn Leu Thr
            20                  25

<210> SEQ ID NO 44
<211> LENGTH: 20
<212> TYPE: PRT
<213> ORGANISM: Porphyromonas gingivalis
<300> PUBLICATION INFORMATION:
<304> VOLUME: 110

```
<305> ISSUE: 2
<306> PAGES: 285-
<307> DATE: 1997

<400> SEQUENCE: 44

Arg Ile Gln Ser Thr Trp Arg Gln Lys Thr Val Asp Leu Pro Ala Gly
 1               5                  10                  15

Thr Lys Tyr Val
            20

<210> SEQ ID NO 45
<211> LENGTH: 20
<212> TYPE: PRT
<213> ORGANISM: Trypanosoma cruzi
<300> PUBLICATION INFORMATION:
<304> VOLUME: 159
<305> ISSUE: 9
<306> PAGES: 4444-
<307> DATE: (1997)

<400> SEQUENCE: 45

Ser His Asn Phe Thr Leu Val Ala Ser Val Ile Ile Glu Ala Pro Ser
 1               5                  10                  15

Gly Asn Thr Cys
            20

<210> SEQ ID NO 46
<211> LENGTH: 21
<212> TYPE: PRT
<213> ORGANISM: Trypanosoma cruzi
<300> PUBLICATION INFORMATION:
<310> PATENT DOCUMENT NUMBER: WO 97/18475

<400> SEQUENCE: 46

Lys Ala Ala Ile Ala Pro Ala Lys Ala Ala Ala Pro Ala Lys Ala
 1               5                  10                  15

Ala Thr Ala Pro Ala
            20

<210> SEQ ID NO 47
<211> LENGTH: 16
<212> TYPE: PRT
<213> ORGANISM: Plasmodium falciparum
<300> PUBLICATION INFORMATION:
<303> JOURNAL: Int. Arch. Allergy Appl. Immunol.
<304> VOLUME: 114
<305> ISSUE: 1
<306> PAGES: 15-

<400> SEQUENCE: 47

Ser Val Gln Ile Pro Lys Val Pro Tyr Pro Asn Gly Ile Val Tyr Cys
 1               5                  10                  15

<210> SEQ ID NO 48
<211> LENGTH: 16
<212> TYPE: PRT
<213> ORGANISM: Plasmodium falciparum
<300> PUBLICATION INFORMATION:
<303> JOURNAL: Int. Arch. Allergy Appl. Immunol.
<304> VOLUME: 114
<305> ISSUE: 1
<306> PAGES: 15-

<400> SEQUENCE: 48

Asp Phe Asn His Tyr Tyr Thr Leu Lys Thr Gly Leu Glu Ala Asp Cys
 1               5                  10                  15
```

-continued

```
<210> SEQ ID NO 49
<211> LENGTH: 16
<212> TYPE: PRT
<213> ORGANISM: Streptococcus sobrinus
<300> PUBLICATION INFORMATION:
<303> JOURNAL: Arch. Oral Biol.
<304> VOLUME: 35
<306> PAGES: Suppl. 475-
<307> DATE: (1990)

<400> SEQUENCE: 49

Lys Pro Arg Pro Ile Tyr Glu Ala Lys Leu Ala Gln Asn Gln Lys Cys
  1               5                  10                  15

<210> SEQ ID NO 50
<211> LENGTH: 17
<212> TYPE: PRT
<213> ORGANISM: Streptococcus sobrinus
<300> PUBLICATION INFORMATION:
<303> JOURNAL: Arch. Oral Biol.
<304> VOLUME: 35
<306> PAGES: Suppl. 475-
<307> DATE: (1990)

<400> SEQUENCE: 50

Ala Lys Ala Asp Tyr Glu Ala Lys Leu Ala Gln Tyr Glu Lys Asp Leu
  1               5                  10                  15

Cys

<210> SEQ ID NO 51
<211> LENGTH: 16
<212> TYPE: PRT
<213> ORGANISM: Lymphocytic choriomeningitis virus
<300> PUBLICATION INFORMATION:
<303> JOURNAL: Proc. Natl. Acad. Sci. U.S.A.
<304> VOLUME: 94
<305> ISSUE: 7
<306> PAGES: 3314-
<307> DATE: (1997)

<400> SEQUENCE: 51

Arg Pro Gln Ala Ser Gly Val Tyr Met Gly Asn Leu Thr Ala Gln Cys
  1               5                  10                  15

<210> SEQ ID NO 52
<211> LENGTH: 9
<212> TYPE: PRT
<213> ORGANISM: Shigella flexneri
<300> PUBLICATION INFORMATION:
<303> JOURNAL: J. Biol. Chem.
<304> VOLUME: 271
<305> ISSUE: 52
<306> PAGES: 33670-
<307> DATE: (1996)

<400> SEQUENCE: 52

Lys Asp Arg Thr Leu Ile Glu Gln Lys
  1               5

<210> SEQ ID NO 53
<211> LENGTH: 15
<212> TYPE: PRT
<213> ORGANISM: respiratory syncytial virus
<300> PUBLICATION INFORMATION:
<304> VOLUME: 234
<305> ISSUE: 1
<306> PAGES: 118-
<307> DATE: 1997
```

```
<400> SEQUENCE: 53

Cys Ser Ile Cys Ser Asn Asn Pro Thr Cys Trp Ala Ile Cys Lys
 1               5                  10                  15

<210> SEQ ID NO 54
<211> LENGTH: 19
<212> TYPE: PRT
<213> ORGANISM: Plasmodium vivax
<300> PUBLICATION INFORMATION:
<303> JOURNAL: Vaccine
<304> VOLUME: 15
<305> ISSUE: 4
<306> PAGES: 377-
<307> DATE: 1997

<400> SEQUENCE: 54

Gly Asp Arg Ala Asp Gly Gln Pro Ala Gly Asp Arg Ala Asp Gly Gln
 1               5                  10                  15

Pro Ala Gly

<210> SEQ ID NO 55
<211> LENGTH: 16
<212> TYPE: PRT
<213> ORGANISM: Clostridium tetani
<300> PUBLICATION INFORMATION:
<303> JOURNAL: Vaccine
<304> VOLUME: 15
<305> ISSUE: 4
<306> PAGES: 377-
<307> DATE: 1997

<400> SEQUENCE: 55

Gln Tyr Ile Lys Ala Asn Ser Lys Phe Ile Gly Ile Thr Glu Leu Cys
 1               5                  10                  15

<210> SEQ ID NO 56
<211> LENGTH: 25
<212> TYPE: PRT
<213> ORGANISM: Entamoeba histolytica
<300> PUBLICATION INFORMATION:
<303> JOURNAL: J. Exp. Med.
<304> VOLUME: 185
<305> ISSUE: 10
<306> PAGES: 1793-
<307> DATE: 1997

<400> SEQUENCE: 56

Val Glu Cys Ala Ser Thr Val Cys Gln Asn Asp Asn Ser Cys Pro Ile
 1               5                  10                  15

Ile Ala Asp Val Glu Lys Cys Asn Gln
                20                  25

<210> SEQ ID NO 57
<211> LENGTH: 34
<212> TYPE: PRT
<213> ORGANISM: Schistosoma japonicum
<300> PUBLICATION INFORMATION:
<303> JOURNAL: Vaccine
<304> VOLUME: 15
<305> ISSUE: 1
<306> PAGES: 79-
<307> DATE: 1997

<400> SEQUENCE: 57

Asp Leu Gln Ser Glu Ile Ser Leu Ser Leu Glu Asn Gly Glu Leu Ile
 1               5                  10                  15

Arg Arg Ala Lys Ser Ala Glu Ser Leu Ala Ser Glu Leu Gln Arg Arg
```

```
                    20                  25                  30

Val Asp

<210> SEQ ID NO 58
<211> LENGTH: 34
<212> TYPE: PRT
<213> ORGANISM: Schistosoma mansoni
<300> PUBLICATION INFORMATION:
<303> JOURNAL: Vaccine
<304> VOLUME: 15
<305> ISSUE: 1
<306> PAGES: 79-
<307> DATE: 1997

<400> SEQUENCE: 58

Asp Leu Gln Ser Glu Ile Ser Leu Ser Leu Glu Asn Ser Glu Leu Ile
 1               5                  10                  15

Arg Arg Ala Lys Ala Ala Glu Ser Leu Ala Ser Asp Leu Gln Arg Arg
                20                  25                  30

Val Asp

<210> SEQ ID NO 59
<211> LENGTH: 63
<212> TYPE: DNA
<213> ORGANISM: Artificial Sequence
<220> FEATURE:
<223> OTHER INFORMATION: Description of Artificial Sequence: MseI
      restriction endonuclease site  inserted into wild type Hepatitis B
      sequence at position 75
<220> FEATURE:
<221> NAME/KEY: CDS
<222> LOCATION: (1)..(63)

<400> SEQUENCE: 59 gct acc tgg gtg ggt gtt aat ttg gaa gat cca gcg tct aga gac cta    48
Ala Thr Trp Val Gly Val Asn Leu Glu Asp Pro Ala Ser Arg Asp Leu
 1               5                  10                  15 gta gtc agt tat gtc                                                63
Val Val Ser Tyr Val
            20

<210> SEQ ID NO 60
<211> LENGTH: 21
<212> TYPE: PRT
<213> ORGANISM: Artificial Sequence

<400> SEQUENCE: 60

Ala Thr Trp Val Gly Val Asn Leu Glu Asp Pro Ala Ser Arg Asp Leu
 1               5                  10                  15

Val Val Ser Tyr Val
            20

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: K inserted
      at amino acid position 75 of Hetatitis B core sequence
<220> FEATURE:
<221> NAME/KEY: CDS
<222> LOCATION: (1)..(39)

<400> SEQUENCE: 61 gct acc tgg gtg ggt gtt aaa aat ttg gaa gat cca gcg tc             41
Ala Thr Trp Val Gly Val Lys Asn Leu Glu Asp Pro Ala
```

-continued

<210> SEQ ID NO 62
<211> LENGTH: 13
<212> TYPE: PRT
<213> ORGANISM: Artificial Sequence

<400> SEQUENCE: 62

Ala Thr Trp Val Gly Val Lys Asn Leu Glu Asp Pro Ala
 1               5                  10

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence:  K inserted
      at amino acid position 76 of hepatitis B core
<220> FEATURE:
<221> NAME/KEY: CDS
<222> LOCATION: (3)..(26)

<400> SEQUENCE: 63 tt aat aaa ttg gaa gat cca gcg tct a                           27
   Asn Lys Leu Glu Asp Pro Ala Ser
     1               5

<210> SEQ ID NO 64
<211> LENGTH: 8
<212> TYPE: PRT
<213> ORGANISM: Artificial Sequence

<400> SEQUENCE: 64

Asn Lys Leu Glu Asp Pro Ala Ser
 1               5

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence:  K inserted
      at position 77 of hepatitis B virus core
<220> FEATURE:
<221> NAME/KEY: CDS
<222> LOCATION: (3)..(26)

<400> SEQUENCE: 65 tt aat ttg aaa gaa gat cca gcg tct a                           27
   Asn Leu Lys Glu Asp Pro Ala Ser
     1               5

<210> SEQ ID NO 66
<211> LENGTH: 8
<212> TYPE: PRT
<213> ORGANISM: Artificial Sequence

<400> SEQUENCE: 66

Asn Leu Lys Glu Asp Pro Ala Ser
 1               5

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence:  K inserted
      at position 78 of hepatitis B core

```
<220> FEATURE:
<221> NAME/KEY: CDS
<222> LOCATION: (3)..(32)

<400> SEQUENCE: 67 tt aat ttg gaa aaa gat cca gcg tct aga gac                           32
   Asn Leu Glu Lys Asp Pro Ala Ser Arg Asp
     1               5                  10

<210> SEQ ID NO 68
<211> LENGTH: 10
<212> TYPE: PRT
<213> ORGANISM: Artificial Sequence

<400> SEQUENCE: 68

Asn Leu Glu Lys Asp Pro Ala Ser Arg Asp
  1               5                  10

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence:  K inserted
      at amino acid position 79 of hepatitis B core
<220> FEATURE:
<221> NAME/KEY: CDS
<222> LOCATION: (3)..(35)

<400> SEQUENCE: 69 tt aat ttg gaa gat aaa cca gcg tct aga gac cta g                     36
   Asn Leu Glu Asp Lys Pro Ala Ser Arg Asp Leu
     1               5                  10

<210> SEQ ID NO 70
<211> LENGTH: 11
<212> TYPE: PRT
<213> ORGANISM: Artificial Sequence

<400> SEQUENCE: 70

Asn Leu Glu Asp Lys Pro Ala Ser Arg Asp Leu
  1               5                  10

<210> SEQ ID NO 71
<211> LENGTH: 39
<212> TYPE: DNA
<213> ORGANISM: Artificial Sequence
<220> FEATURE:
<223> OTHER INFORMATION: Description of Artificial Sequence:  K inserted
      at amino acid position 80 of hepatitis B core
<220> FEATURE:
<221> NAME/KEY: CDS
<222> LOCATION: (3)..(38)

<400> SEQUENCE: 71 tt aat ttg gaa gat cca aaa gcg tct aga gac cta gta g                 39
   Asn Leu Glu Asp Pro Lys Ala Ser Arg Asp Leu Val
     1               5                  10

<210> SEQ ID NO 72
<211> LENGTH: 12
<212> TYPE: PRT
<213> ORGANISM: Artificial Sequence

<400> SEQUENCE: 72

Asn Leu Glu Asp Pro Lys Ala Ser Arg Asp Leu Val
  1               5                  10
```

```
<210> SEQ ID NO 73
<211> LENGTH: 43
<212> TYPE: DNA
<213> ORGANISM: Artificial Sequence
<220> FEATURE:
<223> OTHER INFORMATION: Description of Artificial Sequence:  K inserted
      at amino acid position 81 of hepatitis B core
<220> FEATURE:
<221> NAME/KEY: CDS
<222> LOCATION: (3)..(41)

<400> SEQUENCE: 73 tt aat ttg gaa gat cca gcg aaa tct aga gac cta gta gtc ag           43
   Asn Leu Glu Asp Pro Ala Lys Ser Arg Asp Leu Val Val
     1               5                  10

<210> SEQ ID NO 74
<211> LENGTH: 13
<212> TYPE: PRT
<213> ORGANISM: Artificial Sequence

<400> SEQUENCE: 74

Asn Leu Glu Asp Pro Ala Lys Ser Arg Asp Leu Val Val
  1               5                  10

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence:  K inserted
      at amino acid position 82 of hepatitis B core
<220> FEATURE:
<221> NAME/KEY: CDS
<222> LOCATION: (3)..(44)

<400> SEQUENCE: 75 tt aat ttg gaa gat cca gcg tct aaa aga gac cta gta gtc agt t        45
   Asn Leu Glu Asp Pro Ala Ser Lys Arg Asp Leu Val Val Ser
     1               5                  10

<210> SEQ ID NO 76
<211> LENGTH: 14
<212> TYPE: PRT
<213> ORGANISM: Artificial Sequence

<400> SEQUENCE: 76

Asn Leu Glu Asp Pro Ala Ser Lys Arg Asp Leu Val Val Ser
  1               5                  10

<210> SEQ ID NO 77
<211> LENGTH: 50
<212> TYPE: DNA
<213> ORGANISM: Artificial Sequence
<220> FEATURE:
<223> OTHER INFORMATION: Description of Artificial Sequence:  K inserted
      at amino acid position 83 of hepatitis B core
<220> FEATURE:
<221> NAME/KEY: CDS
<222> LOCATION: (3)..(50)

<400> SEQUENCE: 77 tt aat ttg gaa gat cca gcg tct aga aaa gac cta gta gtc agt tat      47
   Asn Leu Glu Asp Pro Ala Ser Arg Lys Asp Leu Val Val Ser Tyr
     1               5                  10                  15
gtc                                                                  50
Val
```

```
<210> SEQ ID NO 78
<211> LENGTH: 16
<212> TYPE: PRT
<213> ORGANISM: Artificial Sequence

<400> SEQUENCE: 78

Asn Leu Glu Asp Pro Ala Ser Arg Lys Asp Leu Val Val Ser Tyr Val
 1               5                  10                  15

<210> SEQ ID NO 79
<211> LENGTH: 50
<212> TYPE: DNA
<213> ORGANISM: Artificial Sequence
<220> FEATURE:
<223> OTHER INFORMATION: Description of Artificial Sequence:  K inserted
      at amino acid position 84 of hepatitis B core
<220> FEATURE:
<221> NAME/KEY: CDS
<222> LOCATION: (3)..(50)

<400> SEQUENCE: 79 tt aat ttg gaa gat cca gcg tct aga gac aaa cta gta gtc agt tat         47
   Asn Leu Glu Asp Pro Ala Ser Arg Asp Lys Leu Val Val Ser Tyr
    1               5                  10                  15 gtc                                                                    50
Val

<210> SEQ ID NO 80
<211> LENGTH: 16
<212> TYPE: PRT
<213> ORGANISM: Artificial Sequence

<400> SEQUENCE: 80

Asn Leu Glu Asp Pro Ala Ser Arg Asp Lys Leu Val Val Ser Tyr Val
 1               5                  10                  15

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence:  K inserted
      at amino acid position 85 of hepatitis B core
<220> FEATURE:
<221> NAME/KEY: CDS
<222> LOCATION: (2)..(31)

<400> SEQUENCE: 81 c tcg aga gac cta aaa gta gtc agt tat gtc                              31
  Ser Arg Asp Leu Lys Val Val Ser Tyr Val
   1               5                  10

<210> SEQ ID NO 82
<211> LENGTH: 10
<212> TYPE: PRT
<213> ORGANISM: Artificial Sequence

<400> SEQUENCE: 82

Ser Arg Asp Leu Lys Val Val Ser Tyr Val
 1               5                  10

<210> SEQ ID NO 83
<211> LENGTH: 18
<212> TYPE: PRT
<213> ORGANISM: Plasmodium vivax

<400> SEQUENCE: 83
```

-continued

```
Asp Arg Ala Ala Gly Gln Pro Ala Gly Asp Arg Ala Asp Gly Gln Pro
 1               5                  10                  15

Ala Gly

<210> SEQ ID NO 84
<211> LENGTH: 8
<212> TYPE: PRT
<213> ORGANISM: Influenza virus

<400> SEQUENCE: 84

Cys Asn Asn Pro His Arg Ile Leu
 1               5

<210> SEQ ID NO 85
<211> LENGTH: 25
<212> TYPE: PRT
<213> ORGANISM: Influenza virus

<400> SEQUENCE: 85

Cys Pro Lys Tyr Val Lys Gln Asn Thr Leu Lys Leu Ala Thr Gly Met
 1               5                  10                  15

Arg Asn Val Pro Glu Lys Gln Thr Arg
             20                  25

<210> SEQ ID NO 86
<211> LENGTH: 15
<212> TYPE: PRT
<213> ORGANISM: Mycobacterium tuberculosis

<400> SEQUENCE: 86

Ala Val Leu Glu Asp Pro Tyr Ile Leu Leu Val Ser Ser Lys Val
 1               5                  10                  15

<210> SEQ ID NO 87
<211> LENGTH: 15
<212> TYPE: PRT
<213> ORGANISM: Mycobacterium tuberculosis

<400> SEQUENCE: 87

Leu Leu Val Ser Ser Lys Val Ser Thr Val Lys Asp Leu Leu Pro
 1               5                  10                  15

<210> SEQ ID NO 88
<211> LENGTH: 15
<212> TYPE: PRT
<213> ORGANISM: Mycobacterium tuberculosis

<400> SEQUENCE: 88

Leu Leu Pro Leu Leu Glu Lys Val Ile Gly Ala Gly Lys Pro Leu
 1               5                  10                  15

<210> SEQ ID NO 89
<211> LENGTH: 15
<212> TYPE: PRT
<213> ORGANISM: Mycobacterium tuberculosis

<400> SEQUENCE: 89

Ala Ile Leu Thr Gly Gly Gln Val Ile Ser Glu Glu Val Gly Leu
 1               5                  10                  15

<210> SEQ ID NO 90
<211> LENGTH: 15
<212> TYPE: PRT
```

<213> ORGANISM: Mycobacterium tuberculosis

<400> SEQUENCE: 90

Ile Ala Phe Asn Ser Gly Leu Glu Pro Gly Val Val Ala Glu Lys
1 5 10 15

<210> SEQ ID NO 91
<211> LENGTH: 18
<212> TYPE: PRT
<213> ORGANISM: Mycobacterium tuberculosis

<400> SEQUENCE: 91

Ala Arg Arg Gly Leu Glu Arg Gly Leu Asn Ala Leu Ala Asp Ala Val
1 5 10 15

Lys Val

<210> SEQ ID NO 92
<211> LENGTH: 14
<212> TYPE: PRT
<213> ORGANISM: Mycobacterium tuberculosis

<400> SEQUENCE: 92

Glu Lys Ile Gly Ala Glu Leu Val Lys Glu Val Ala Lys Lys
1 5 10

<210> SEQ ID NO 93
<211> LENGTH: 17
<212> TYPE: PRT
<213> ORGANISM: Mycobacterium tuberculosis

<400> SEQUENCE: 93

Gly Leu Lys Arg Gly Ile Glu Lys Ala Val Glu Lys Val Thr Glu Thr
1 5 10 15

Leu

<210> SEQ ID NO 94
<211> LENGTH: 15
<212> TYPE: PRT
<213> ORGANISM: Mycobacterium tuberculosis

<400> SEQUENCE: 94

Ile Glu Asp Ala Val Arg Asn Ala Lys Ala Ala Val Glu Glu Gly
1 5 10 15

<210> SEQ ID NO 95
<211> LENGTH: 20
<212> TYPE: PRT
<213> ORGANISM: Feline leukemia virus

<400> SEQUENCE: 95

Cys Asp Ile Ile Gly Asn Thr Trp Asn Pro Ser Asp Gln Glu Pro Phe
1 5 10 15

Pro Gly Tyr Gly
20

<210> SEQ ID NO 96
<211> LENGTH: 21
<212> TYPE: PRT
<213> ORGANISM: Feline leukemia virus

<400> SEQUENCE: 96

Cys Ile Gly Thr Val Pro Lys Thr His Gln Ala Leu Cys Asn Glu Thr
1 5 10 15

Gln Gln Gly His Thr
            20

<210> SEQ ID NO 97
<211> LENGTH: 13
<212> TYPE: PRT
<213> ORGANISM: Feline leukemia virus

<400> SEQUENCE: 97

Gly Asn Tyr Ser Asn Gln Thr Asn Pro Pro Pro Ser Cys
  1               5                  10

<210> SEQ ID NO 98
<211> LENGTH: 22
<212> TYPE: PRT
<213> ORGANISM: Feline leukemia virus

<400> SEQUENCE: 98

Thr Asp Ile Gln Ala Leu Glu Glu Ser Ile Ser Ala Leu Glu Lys Ser
  1               5                  10                  15

Leu Thr Ser Leu Ser Glu
            20

<210> SEQ ID NO 99
<211> LENGTH: 14
<212> TYPE: PRT
<213> ORGANISM: Feline leukemia virus

<400> SEQUENCE: 99

Ala Lys Leu Arg Glu Arg Leu Lys Gln Arg Gln Gln Leu Phe
  1               5                  10

<210> SEQ ID NO 100
<211> LENGTH: 23
<212> TYPE: PRT
<213> ORGANISM: Feline leukemia virus

<400> SEQUENCE: 100

Asp Ser Gln Gln Gly Trp Phe Glu Gly Trp Phe Asn Lys Ser Pro Trp
  1               5                  10                  15

Phe Thr Thr Leu Ile Ser Ser
            20

<210> SEQ ID NO 101
<211> LENGTH: 18
<212> TYPE: PRT
<213> ORGANISM: Feline leukemia virus

<400> SEQUENCE: 101

Gln Val Met Thr Ile Thr Pro Pro Gln Ala Met Gly Pro Asn Leu Val
  1               5                  10                  15

Leu Pro

<210> SEQ ID NO 102
<211> LENGTH: 17
<212> TYPE: PRT
<213> ORGANISM: Feline leukemia virus

<400> SEQUENCE: 102

Asp Gln Lys Pro Pro Ser Arg Gln Ser Gln Ile Glu Ser Arg Val Thr
  1               5                  10                  15

Pro

```
<210> SEQ ID NO 103
<211> LENGTH: 15
<212> TYPE: PRT
<213> ORGANISM: Feline leukemia virus

<400> SEQUENCE: 103

Arg Arg Gly Leu Asp Ile Leu Phe Leu Gln Glu Gly Gly Leu Cys
 1               5                  10                  15

<210> SEQ ID NO 104
<211> LENGTH: 25
<212> TYPE: PRT
<213> ORGANISM: Feline leukemia virus

<400> SEQUENCE: 104

Gln Glu Gly Gly Leu Cys Ala Ala Leu Glu Glu Cys Gln Ile Gly Gly
 1               5                  10                  15

Leu Cys Ala Ala Leu Lys Glu Glu Cys
            20                  25

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Cytochrome
      P-450 fragment
<300> PUBLICATION INFORMATION:
<303> JOURNAL: Science
<304> VOLUME: 228
<306> PAGES: 1436-1440
<307> DATE: 1985

<400> SEQUENCE: 105

Asn Ala Asn Pro Asn Ala Asn Pro Asn Ala Asn Pro
 1               5                  10

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence:  Cytochrome
      P-450 fragment

<400> SEQUENCE: 106

Cys Met Gln Leu Arg Ser
 1               5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence:  Cytochrome
      P-450 fragment

<400> SEQUENCE: 107

Cys Arg Phe Ser Ile Asn
 1               5

<210> SEQ ID NO 108
<211> LENGTH: 5
<212> TYPE: PRT
<213> ORGANISM: Artificial Sequence
<220> FEATURE:
```

-continued

```
<223> OTHER INFORMATION: Description of Artificial Sequence:  Cytochrome
      P-450 fragment

<400> SEQUENCE: 108

Cys Ala Val Pro Arg
 1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence:  Cytochrome
      P-450 fragment

<400> SEQUENCE: 109

Cys Ile Pro Arg Ser
 1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence:  Cytochrome
      P-450 fragment

<400> SEQUENCE: 110

Cys Phe Ile Pro Val
 1               5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence:  Cytochrome
      P-450 fragment

<400> SEQUENCE: 111

Cys Thr Val Ser Gly Ala
 1               5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence:  Cytochrome
      P-450 fragment

<400> SEQUENCE: 112

Cys Thr Leu Ser Gly Glu
 1               5

<210> SEQ ID NO 113
<211> LENGTH: 12
<212> TYPE: PRT
<213> ORGANISM: Plasmodium knowlesi

<400> SEQUENCE: 113

Gln Ala Gln Gly Asp Gly Ala Asn Ala Gly Gln Pro
 1               5                  10
```